US012611403B2

(12) United States Patent
Zhang et al.

(10) Patent No.: US 12,611,403 B2
(45) Date of Patent: Apr. 28, 2026

(54) COMBINED PHARMACEUTICAL COMPOSITION OF C-MET KINASE INHIBITOR AND ANTI-PD-L1 ANTIBODY

(71) Applicants: CHIA TAI TIANQING PHARMACEUTICAL GROUP CO., LTD., Lianyungang (CN); TIANJIN MEDICAL UNIVERSITY CANCER INSTITUTE AND HOSPITAL, Tianjin (CN)

(72) Inventors: Xiquan Zhang, Lianyungang (CN); Xunqiang Wang, Lianyungang (CN); Ding Yu, Lianyungang (CN); Tao Liu, Lianyungang (CN); Xiaole Zhan, Lianyungang (CN); Naiying Wu, Lianyungang (CN)

(73) Assignees: CHIA TAI TIANQING PHARMACEUTICAL GROUP CO., LTD, Lianyungang (CN); TIANJIN MEDICAL UNIVERSITY CANCER INSTITUTE AND HOSPITAL, Jianjin (CN)

( * ) Notice: Subject to any disclaimer, the term of this patent is extended or adjusted under 35 U.S.C. 154(b) by 627 days.

(21) Appl. No.: 17/999,028

(22) PCT Filed: Jun. 1, 2021

(86) PCT No.: PCT/CN2021/097776
§ 371 (c)(1),
(2) Date: Nov. 16, 2022

(87) PCT Pub. No.: WO2021/244551
PCT Pub. Date: Dec. 9, 2021

(65) Prior Publication Data
US 2023/0263795 A1 Aug. 24, 2023

(30) Foreign Application Priority Data

Jun. 2, 2020 (CN) .......................... 202010489236.1
Jun. 2, 2020 (CN) .......................... 202010489252.0

(51) Int. Cl.
A61K 31/47 (2006.01)
A61K 39/00 (2006.01)
A61K 39/395 (2006.01)
A61P 35/00 (2006.01)

(52) U.S. Cl.
CPC .......... *A61K 31/47* (2013.01); *A61K 39/3955* (2013.01); *A61P 35/00* (2018.01); *A61K 2039/545* (2013.01)

(58) Field of Classification Search
None
See application file for complete search history.

(56) References Cited

U.S. PATENT DOCUMENTS 8,420,645 B2 4/2013 Weng et al.
2019/0224200 A1 7/2019 Santos et al.

FOREIGN PATENT DOCUMENTS

| CN | 103328447 | 9/2013 |
| CN | 107001463 | 8/2017 |
| JP | 2016155778 | 9/2016 |
| WO | 2012034055 | 3/2012 |
| WO | 2016022630 A1 | 2/2016 |
| WO | 2016040892 | 3/2016 |
| WO | 2016061142 A1 | 4/2016 |
| WO | 2019161320 | 8/2019 |

OTHER PUBLICATIONS

Herold et al (Sci Rep. Sep. 25, 2017;7(1):12276) (Year: 2017).*
Rabia et al (Understanding and overcoming trade-offs between antibody affinity, specificity, stability and solubility. Biochemical engineering journal, 137, 365â374, 2018) (Year: 2018).*
Rudikoff et al (Single amino acid substitution altering antigen-binding specificity. Proc Natl Acad Sci U S A. Mar. 1982;79(6):1979-83 ) (Year: 1979).*
Vajdos et al (Comprehensive functional maps of the antigen-binding site of an anti-ErbB2 antibody obtained with shotgun scanning mutagenesis. Journal of molecular biology, 320(2), 415â428, 2022) (Year: 2022).*
International Search Report and Written Opinion, issued in International Patent Application No. PCT/CN2021/097776, mail date Sep. 1, 2021.
Sonnenberg et al., J. Cell Biol. 123 223-235. 1993.
Matsumato et al., Crit Rev Oncog 3:27-54, 1992 (Abstract).
Stroker et al. Nature 327:239-242, 1987 (Abstract).
Gettinger S et al. 2018 Clin oncol. 36(17): 1675-1684.
Viswanath Gunda et al: "Anti-PD-1/PD-L1 therapy augments lenvatinib's efficacy by favorably altering the immune microenvironment of murine anaplastic thyroid cancer", International Journal of Cancer, John Wiley & Sons, Inc, US, vol. 144, No. 9, Jan. 24, 2019 (Jan. 24, 2019), pp. 2266-2278.
Ahn Hyun Kyung et al: "MET Receptor Tyrosine Kinase Regulates the Expression of Co-Stimulatory and Co-Inhibitory Molecules in Tumor Cells and Contributes to PO•L 1-Mediated Suppression of Immune Cell Function", International journal of molecular sciences, vol. 20, No. 17, Sep. 1, 2019 (Sep. 1, 2019), p. 4287.

(Continued)

*Primary Examiner* — Zachariah Lucas
*Assistant Examiner* — Sarah A Alsomairy
(74) *Attorney, Agent, or Firm* — Ping Wang; Kalos Athena Wang PLLC

(57) ABSTRACT

Provided are a combined pharmaceutical composition of an anti-PD-L1 antibody and a c-Met kinase inhibitor, specifically, a combined pharmaceutical composition of an anti-PD-L1 antibody and N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide, and the use of the combined pharmaceutical composition in the treatment of cancers, in particular, gastric cancer or liver cancer.

20 Claims, No Drawings
Specification includes a Sequence Listing.

(56)           References Cited

OTHER PUBLICATIONS

Hong David et al: "A Phase 1 b/2 Study of the Bruton Tyrosine Kinase Inhibitor Ibrutinib and the PD-L 1 Inhibitor Durvalumab in Patients with Pretreated Solid Tumors", Oncology : international journal of cancer research and treatment, vol. 97, No. 2, Jan. 1, 2019 (Jan. 1, 2019), pp. 102-111.
Garcia-Aranda Marilina et al: "Targeting Protein Kinases to Enhance the Response to anti-PD-1/PD-L 1 Immunotherapy", International Journal of Molecular Sciences, vol. 20, No. 9, May 9, 2019 (May 9, 2019), p. 2296.
Pubchem: "Capmatinib | C23H17FN60 | CID 25145656—PubChem", Jun. 19, 2024 (Jun. 19, 2024), pp. 1-28.

* cited by examiner

1

COMBINED PHARMACEUTICAL COMPOSITION OF C-MET KINASE INHIBITOR AND ANTI-PD-L1 ANTIBODY

CROSS-REFERENCE TO RELATED APPLICATIONS

The present disclosure claims priority to the Chinese Patent Application No. 202010489252.0 filed on Jun. 2, 2020 and the Chinese Patent Application No. 202010489236.1 filed on Jun. 2, 2020, the content of which is incorporated herein by reference in its entirety and for all purposes.

TECHNICAL FIELD

The present disclosure relates to the technical field of pharmaceuticals, and particularly to a combined pharmaceutical composition of N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide and an anti-PD-L1 antibody, and use of the combined pharmaceutical composition for treating cancers, in particular, gastric cancer or liver cancer.

BACKGROUND c-Met kinase is a prototype member of a subfamily of heterodimeric receptor tyrosine kinases (RTKs), which include Met, Ron and Sea. The anti-angiogenic and anti-proliferative activities of c-Met make it an attractive target. The endogenous ligand for c-Met is hepatocyte growth factor (HGF), which is also known as scatter factor (SF) because it can interfere with colony formation in vitro. HGF is a derivatized cytokine that induces receptor activation by autophosphorylation resulting in increased receptor-dependent signaling in normal cells and tumor cells (Sonnenberg et al., *J. Cell Biol.* 123:223-235, 1993; Matsumato et al., *Crit. Rev. Oncog.* 3:27-54, 1992; Stoker et al. *Nature* 327:239-242, 1987). Anti-HGF antibodies or HGF antagonists have also been shown to inhibit tumor metastasis.

WO2012034055 discloses N-(4-((7-((1-(cyclopentylamino)cyclopropyl)methoxy)-6-methoxyquinolin-4-yl)oxy)-3-fluorophenyl)-N-(4-fluorophenyl)cyclopropane-1,1-dicarboxamide (hereinafter referred to as the compound of formula (I)) as a c-Met kinase inhibitor and use thereof for inhibiting tyrosine kinase activity,

2

PD-1 immune checkpoint is an inhibitory cell surface receptor, and the expression of its corresponding ligand, PD-L1, can be up-regulated on the surfaces of tumor cells and immune cells in the tumor environment, thereby allowing tumor cells to escape from the attack by immune cells. Anti-PD-1 or PD-L1 antibodies can be used to block this response, producing an anti-tumor effect. Immune checkpoint inhibitors directed against the PD-1/PD-L1 pathway have significantly improved the prognosis of patients with non-small cell lung cancer, but the therapeutic effects are poor in most patients due to primary drug resistance. In a study using the PD-1/PD-L1 pathway inhibitor Nivolumab (Gettinger S et al. (2018) *ClinOncol.* 36(17):1675-1684), patients with low and no PD-L1 expression accounted for 80.1% (55/68), and the survival rate of these patients was also significantly lower than that of patients with high PD-L1 expression. The analysis showed that there may be primary drug resistance in patients, resulting in poor immunotherapeutic effect. Thus, there is an urgent need to find other therapeutic approaches to overcome the problem of immunotherapy resistance.

BRIEF SUMMARY

In one aspect, the present disclosure provides a combined pharmaceutical composition, which comprises an anti-PD-L1 antibody and a compound of formula (I) or a pharmaceutically acceptable salt thereof, wherein the anti-PD-L1 antibody comprises the following amino acid sequences: a heavy chain CDR1 region having at least 80% homology to an amino acid sequence set forth in SEQ ID NO: 1 or SEQ ID NO: 4; a heavy chain CDR2 region having at least 80% homology to an amino acid sequence set forth in SEQ ID NO: 2 or SEQ ID NO: 5; a heavy chain CDR3 region having at least 80% homology to an amino acid sequence set forth in SEQ ID NO: 3 or SEQ ID NO: 6; a light chain CDR1 region having at least 80% homology to an amino acid sequence set forth in SEQ ID NO: 7 or SEQ ID NO: 10; a light chain CDR2 region having at least 80% homology to an amino acid sequence set forth in SEQ ID NO: 8 or SEQ ID NO: 11; and a light chain CDR3 region having at least 80% homology to an amino acid sequence set forth in SEQ ID NO: 9 or SEQ ID NO: 12;

formula (I)

formula (I)

In some embodiments, the combined pharmaceutical composition is a combined pharmaceutical composition for use in treating cancer.

In some embodiments, the combined pharmaceutical composition is packaged in a kit further comprising an instruction for use of the anti-PD-L1 antibody in combination with the compound of formula (I) or the pharmaceutically acceptable salt thereof for treating cancer in a patient.

In some embodiments, in the combined pharmaceutical composition, the anti-PD-L1 antibody and the compound of formula (I) or the pharmaceutically acceptable salt thereof are packaged separately in respective kits further comprising an instruction for use of the anti-PD-L1 antibody in combination with the compound of formula (I) or the pharmaceutically acceptable salt thereof for treating cancer in a patient.

In some specific embodiments, the cancer is liver cancer or gastric cancer.

In some specific embodiments, the liver cancer is hepatocellular carcinoma and the gastric cancer is gastric adenocarcinoma or gastroesophageal junction adenocarcinoma.

In some embodiments, the combined pharmaceutical composition comprises a pharmaceutical composition of the anti-PD-L1 antibody and a pharmaceutical composition of the compound of formula (I) or the pharmaceutically acceptable salt thereof.

In some embodiments of the present disclosure, in the combined pharmaceutical composition, the anti-PD-L1 antibody and the compound of formula (I) or the pharmaceutically acceptable salt thereof are each in the form of a pharmaceutical composition and can be administered simultaneously, sequentially or at intervals.

In some embodiments of the present disclosure, the combined pharmaceutical composition is a fixed combination.

In some embodiments, the fixed composition is in the form of a solid pharmaceutical composition or a liquid pharmaceutical composition.

In some embodiments of the present disclosure, the combined pharmaceutical composition is a non-fixed combination. In some embodiments, the anti-PD-L1 antibody and the compound of formula (I) or the pharmaceutically acceptable salt thereof in the non-fixed combination are each in the form of a pharmaceutical composition.

In some specific embodiments, in the combined pharmaceutical composition, the anti-PD-L1 antibody comprises: a heavy chain CDR1 region set forth in SEQ ID NO: 1 or SEQ ID NO: 4; a heavy chain CDR2 region set forth in SEQ ID NO: 2 or SEQ ID NO: 5; a heavy chain CDR3 region set forth in SEQ ID NO: 3 or SEQ ID NO: 6; a light chain CDR1 region set forth in SEQ ID NO: 7 or SEQ ID NO: 10; a light chain CDR2 region set forth in SEQ ID NO: 8 or SEQ ID NO: 11; and a light chain CDR3 region set forth in SEQ ID NO: 9 or SEQ ID NO: 12.

In some specific embodiments, in the combined pharmaceutical composition, the anti-PD-L1 antibody comprises: a heavy chain CDR1 region having an amino acid sequence set forth in SEQ ID NO: 1; a heavy chain CDR2 region having an amino acid sequence set forth in SEQ ID NO: 2; a heavy chain CDR3 region having an amino acid sequence set forth in SEQ ID NO: 3; a light chain CDR1 region having an amino acid sequence set forth in SEQ ID NO: 7; a light chain CDR2 region having an amino acid sequence set forth in SEQ ID NO: 8; and a light chain CDR3 region having an amino acid sequence set forth in SEQ ID NO: 9.

In some specific embodiments, in the combined pharmaceutical composition, the anti-PD-L1 antibody comprises: a heavy chain CDR1 region set forth in SEQ ID NO: 4; a heavy chain CDR2 region set forth in SEQ ID NO: 5; a heavy chain CDR3 region set forth in SEQ ID NO: 6; a light chain CDR1 region set forth in SEQ ID NO: 10; a light chain CDR2 region set forth in SEQ ID NO: 11; and a light chain CDR3 region set forth in SEQ ID NO: 12.

In some specific embodiments, in the combined pharmaceutical composition, the anti-PD-L1 antibody or the antigen-binding fragment thereof is a 13C5, 5G11, ch13C5-hIgG1, ch13C5-hIgG4, ch5G11-hIgG1, ch5G11-hIgG4, hu13C5-hIgG1, hu13C5-hIgG4, hu5G11-hIgG1 or hu5G11-hIgG4 monoclonal antibody or an antigen-binding fragment thereof (see WO2016022630 or CN107001463A).

In some specific embodiments, in the combined pharmaceutical composition, the anti-PD-L1 antibody comprises: a heavy chain complementarity determining region (CDR) selected from the group consisting of heavy chain CDRs of antibodies 13C5 and 5G11; and a light chain CDR selected from the group consisting of light chain CDRs of antibodies 13C5 and 5G11. In one embodiment, the present disclosure provides an anti-PD-L1 antibody, which comprises: a heavy chain variable region selected from the group consisting of heavy chain variable regions of chimeric antibodies ch5G11-hIgG1, ch5G11-hIgG4, ch13C5-hIgG1 and ch13C5-hIgG4; and a light chain variable region selected from the group consisting of light chain variable regions of chimeric antibodies ch5G11-hIgG1, ch5G11-hIgG4, ch13C5-hIgG1 and ch13C5-hIgG4. In one embodiment, the present disclosure provides an anti-PD-L1 antibody, which comprises a heavy chain variable region selected from the group consisting of heavy chain variable regions of humanized antibodies hu13C5-hIgG1, hu13C5-hIgG4, hu5G11-hIgG1 and hu5G11-hIgG4; and a light chain variable region selected from the group consisting of light chain variable regions of humanized antibodies hu13C5-hIgG1, hu13C5- hIgG4, hu5G11-hIgG1 and hu5G11-hIgG4. Reference can be made to the description of the patent WO2016022630 or CN107001463A: 13C5, ch13C5-hIgG1, ch13C5-hIgG4, hu13C5-hIgG1 or hu13C5-hIgG4 comprises an HCDR1 sequence of SYGMS (SEQ ID NO: 4), an HCDR2 sequence of SISSGGSTYYPDSVKG (SEQ ID NO: 5), an HCDR3 sequence of GYDSGFAY (SEQ ID NO: 6), an LCDR1 sequence of ASQSVSTSSSSFMH (SEQ ID NO: 10), an LCDR2 sequence of YASNLES (SEQ ID NO: 11), and an LCDR3 sequence of QHSWEIPYT (SEQ ID NO: 12); 5G11, ch5G11-hIgG1, ch5G11-hIgG4, hu5G11-hIgG1 or hu5G11-hIgG4 comprises an HCDR1 sequence of TYGVH (SEQ ID NO: 1), an HCDR2 sequence of VIWRGVTTDY-NAAFMS (SEQ ID NO: 2), an HCDR3 sequence of LGFYAMDY (SEQ ID NO: 3), an LCDR1 sequence of KASQSVSNDVA (SEQ ID NO: 7), an LCDR2 sequence of YAANRYT (SEQ ID NO: 8), and an LCDR3 sequence of QQDYTSPYT (SEQ ID NO: 9).

In some embodiments, in the combined pharmaceutical composition, the anti-PD-L1 antibody comprises the following amino acid sequences: a heavy chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 1 or SEQ ID NO: 4; a heavy chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 2 or SEQ ID NO: 5; a heavy chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 3 or SEQ ID NO: 6; a light chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 7 or SEQ ID NO: 10; a light chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 8 or SEQ ID NO: 11; and a light chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 9 or SEQ ID NO: 12.

In some embodiments, in the combined pharmaceutical composition, the anti-PD-L1 antibody comprises the following amino acid sequences: a heavy chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 1; a heavy chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 2; a heavy chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 3; a light chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 7; a light chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 8; and a light chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 9.

In some embodiments, in the combined pharmaceutical composition, the anti-PD-L1 antibody comprises the following amino acid sequences: a heavy chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 4; a heavy chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 5; a heavy chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 6; a light chain CDR1 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 10; a light chain CDR2 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 11; and a light chain CDR3 region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 12.

Preferably, the anti-PD-L1 antibody disclosed herein comprises the following amino acid sequences: a heavy chain variable region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 13 or SEQ ID NO: 14; and a light chain variable region having at least 80% (e.g., 81%, 82%, 83%, 84%, 85%, 86%, 87%, 88%, 89%, 90%, 91%, 92%, 93%, 94%, 95%, 96%, 97%, 98%, 99% or 100%) homology to an amino acid sequence set forth in SEQ ID NO: 15 or SEQ ID NO: 16.

In one specific embodiment, in the combined pharmaceutical composition, the anti-PD-L1 antibody comprises the following amino acid sequences: a heavy chain variable region set forth in SEQ ID NO: 13, and a light chain variable region set forth in SEQ ID NO: 15.

In one specific embodiment, in the combined pharmaceutical composition, the anti-PD-L1 antibody comprises the following amino acid sequences: a heavy chain variable region set forth in SEQ ID NO: 14, and a light chain variable region set forth in SEQ ID NO: 16.

In one specific embodiment, in the combined pharmaceutical composition, the anti-PD-L1 antibody comprises: a heavy chain amino acid sequence set forth in SEQ ID NO: 17, and a light chain amino acid sequence set forth in SEQ ID NO: 18.

In one specific embodiment, in the combined pharmaceutical composition, the anti-PD-L1 antibody comprises: a heavy chain amino acid sequence set forth in SEQ ID NO: 19, and a light chain amino acid sequence set forth in SEQ ID NO: 20.

In one specific embodiment, in the combined pharmaceutical composition, the anti-PD-L1 antibody comprises: a heavy chain amino acid sequence set forth in SEQ ID NO: 21, and a light chain amino acid sequence set forth in SEQ ID NO: 18.

In one preferred embodiment of the present disclosure, in the combined pharmaceutical composition, the anti-PD-L1 antibody is hu5G11-hIgG1, which comprises a heavy chain amino acid sequence set forth in SEQ ID NO: 17 and a light chain amino acid sequence set forth in SEQ ID NO: 18.

In some embodiments, the combined pharmaceutical composition comprises about 20 mg to about 2400 mg of the anti-PD-L1 antibody.

In some embodiments, the combined pharmaceutical composition comprises about 600 mg to about 2400 mg of the anti-PD-L1 antibody.

In some embodiments, the combined pharmaceutical composition comprises about 1000 mg to about 1500 mg of the anti-PD-L1 antibody.

In some specific embodiments, the combined pharmaceutical composition comprises about 100 mg, about 300 mg, about 600 mg, about 900 mg, about 1000 mg, about 1200 mg, about 1500 mg, about 1800 mg, about 2100 mg, or about 2400 mg of the anti-PD-L1 antibody.

In some specific embodiments, the combined pharmaceutical composition comprises about 1200 mg of the anti-PD-L1 antibody.

In some embodiments, in the combined pharmaceutical composition, the pharmaceutical composition of the anti-PD-L1 antibody is in a single dose or in multiple doses. In some specific embodiments, in the combined pharmaceutical composition, the pharmaceutical composition of the anti-PD-L1 antibody is in multiple doses.

In some embodiments, in the combined pharmaceutical composition, the pharmaceutical composition of the anti-PD-L1 antibody has a concentration of about 1-150 mg/mL, about 10-60 mg/mL, about 10 mg/mL, or about 30 mg/mL (w/v).

In some specific embodiments, in the combined pharmaceutical composition, the anti-PD-L1 antibody is prepared as a pharmaceutical composition suitable for administration at a dose of 1 mg/kg, 2 mg/kg, 3 mg/kg, 5 mg/kg, 6 mg/kg, 9 mg/kg, 10 mg/kg, 15 mg/kg, 20 mg/kg or 30 mg/kg body weight.

In certain embodiments, in the combined pharmaceutical composition, the dose of the anti-PD-L1 antibody is a fixed dose in the pharmaceutical composition.

In some embodiments, in the combined pharmaceutical composition, the content of the anti-PD-L1 antibody is a daily dose.

In some embodiments, in the combined pharmaceutical composition, the content of the anti-PD-L1 antibody is a flat dose.

In some embodiments, in the combined pharmaceutical composition, the content of the anti-PD-L1 antibody is a dose for one 21-day cycle.

In one specific embodiment of the present disclosure, in the combined pharmaceutical composition, the anti-PD-L1 antibody is present in the form of a pharmaceutical composition comprising about 1-150 mg/mL (m/v) anti-PD-L1 antibody, 3-50 mM buffer, 2-150 mg/mL isotonicity modifier/stabilizer and 0.01-0.8 mg/mL surfactant, and having a pH of about 4.5-6.8.

In another specific embodiment of the present disclosure, in combined pharmaceutical composition, the pharmaceutical composition of the anti-PD-L1 antibody comprises: (a) the anti-PD-L1 antibody at a concentration of about 10 mg/mL or about 30 mg/mL (w/v), (b) sucrose at a concentration of about 80 mg/mL (w/v), (c) polysorbate 80 at a concentration of about 0.2 mg/mL (w/v), (d) histidine at a molar concentration of about 10 mM, and (e) optionally a suitable amount of hydrochloric acid for adjusting the pH of the composition to about 5.5.

In one specific embodiment of the present disclosure, in the combined pharmaceutical composition, the pharmaceutical composition of the anti-PD-L1 antibody comprises: (a) hu5G11-hIgG1 at a concentration of about 10 mg/mL or about 30 mg/mL (w/v), (b) sucrose at a concentration of about 80 mg/mL (w/v), (c) polysorbate 80 at a concentration of about 0.2 mg/mL (w/v), (d) histidine at a molar concentration of about 10 mM, and (e) optionally a suitable amount of hydrochloric acid for adjusting the pH of the composition to about 5.5.

In some embodiments, in the combined pharmaceutical composition, the pharmaceutical composition of the anti-PD-L1 antibody is a water-soluble injection, including but not limited to a water-soluble formulation without lyophilization or a water-soluble formulation reconstituted from a lyophilized powder. In other embodiments, in the combined pharmaceutical composition, the pharmaceutical composition of the anti-PD-L1 antibody is a lyophilized formulation. The lyophilized formulation refers to a formulation prepared by subjecting an aqueous solution to a lyophilization process. Lyophilization is a stabilization process, in which a substance is first frozen, and then the amount of a solvent is reduced by sublimation (primary drying process) and then by desorption (secondary drying process) until the amount of the solvent is reduced to a value that no longer supports a biological activity or a chemical reaction.

In some embodiments, in the combined pharmaceutical composition, the pharmaceutical composition of the anti-PD-L1 antibody is a hu5G11-hIgG1 injection with a strength of 100 mg/10 mL or 600 mg/20 mL.

The pharmaceutical composition formulation of the anti-PD-L1 antibody provided herein contains no more than 1.1%, preferably no more than 0.9%, and more preferably no more than 0.5%, aggregates after being stored at 2-8° C. or 25° C. for at least 6 months.

In some specific embodiments, the combined pharmaceutical composition comprises the pharmaceutical composition of about 20 mg to about 2400 mg, about 600 mg to about 2400 mg, or about 1000 mg to about 1500 mg of the anti-PD-L1 antibody in multiple doses, wherein the content of the anti-PD-L1 antibody is a flat dose; the multiple doses consist of single doses, wherein the single dose is the pharmaceutical composition of 100 mg or 600 mg of the anti-PD-L1 antibody.

In some specific embodiments, the combined pharmaceutical composition comprises the pharmaceutical composition of about 100 mg, about 300 mg, about 600 mg, about 900 mg, about 1000 mg, about 1200 mg, about 1500 mg, about 1800 mg, about 2100 mg, or about 2400 mg of the anti-PD-L1 antibody in multiple doses, wherein the content of the anti-PD-L1 antibody is a flat dose; the multiple doses consist of single doses, wherein the single dose is the pharmaceutical composition of 100 mg or 600 mg of the anti-PD-L1 antibody.

In some specific embodiments, the combined pharmaceutical composition comprises the pharmaceutical composition of about 1200 mg of the anti-PD-L1 antibody in multiple doses, wherein the content of the anti-PD-L1 antibody is a flat dose; the multiple doses consist of single doses, wherein the single dose is the pharmaceutical composition of 100 mg or 600 mg of the anti-PD-L1 antibody.

In some embodiments, the combined pharmaceutical composition comprises 90 mg to 180 mg of the compound of formula (I) or the pharmaceutically acceptable salt thereof.

In some embodiments, the combined pharmaceutical composition comprises 90 mg to 120 mg, 90 mg to 150 mg, 120 mg to 150 mg, 120 mg to 180 mg, or 150 mg to 180 mg of the compound of formula (I) or the pharmaceutically acceptable salt thereof.

In some embodiments, the combined pharmaceutical composition comprises 90 mg, 120 mg, 150 mg, or 180 mg of the compound of formula (I) or the pharmaceutically acceptable salt thereof.

In some embodiments, the combined pharmaceutical composition comprises 120 mg or 150 mg of the compound of formula (I) or the pharmaceutically acceptable salt thereof.

In some embodiments, in the combined pharmaceutical composition, the pharmaceutical composition of the compound of formula (I) or the pharmaceutically acceptable salt thereof is in a single dose or in multiple doses.

In some embodiments, in the combined pharmaceutical composition, the pharmaceutical composition of the compound of formula (I) or the pharmaceutically acceptable salt thereof is in multiple doses.

In some embodiments, the combined pharmaceutical composition comprises the pharmaceutical composition of 30 mg or 60 mg of the compound of formula (I) or the pharmaceutically acceptable salt thereof in a single dose.

In some embodiments, in the combined pharmaceutical composition, the pharmaceutical composition of the compound of formula (I) or the pharmaceutically acceptable salt thereof is in multiple doses consisting of single doses, wherein the single dose is the pharmaceutical composition of 30 mg or 60 mg of the compound of formula (I) or the pharmaceutically acceptable salt thereof.

In some embodiments, in the combined pharmaceutical composition, the content of the compound of formula (I) or the pharmaceutically acceptable salt thereof is a daily dose.

In some embodiments, in the combined pharmaceutical composition, the content of the compound of formula (I) or the pharmaceutically acceptable salt thereof is a once-daily dose.

In some embodiments, in the combined pharmaceutical composition, the content of the compound of formula (I) or the pharmaceutically acceptable salt thereof is a once-daily dose, and the pharmaceutical composition of the compound of formula (I) or the pharmaceutically acceptable salt thereof is in a single dose or in multiple doses.

In some specific embodiments, the combined pharmaceutical composition comprises the pharmaceutical composition of 90 mg to 180 mg, 90 mg to 120 mg, 90 mg to 150 mg, 120 mg to 150 mg, 120 mg to 180 mg, or 150 mg to 180 mg of the compound of formula (I) or the pharmaceutically acceptable salt thereof in multiple doses wherein the content of the compound of formula (I) or the pharmaceutically acceptable salt thereof is a once-daily dose; the multiple doses consist of single doses, wherein the single dose is the pharmaceutical composition of 30 mg or 60 mg of the compound of formula (I) or the pharmaceutically acceptable salt thereof.

In some specific embodiments, the combined pharmaceutical composition comprises the pharmaceutical composition of 90 mg, 120 mg, 150 mg, or 180 mg of the compound of formula (I) or the pharmaceutically acceptable salt thereof in multiple doses, wherein the content of the compound of formula (I) or the pharmaceutically acceptable salt thereof is a once-daily dose; the multiple doses consist of single doses, wherein the single dose is the pharmaceutical composition of 30 mg or 60 mg of the compound of formula (I) or the pharmaceutically acceptable salt thereof.

In some preferred embodiments, the combined pharmaceutical composition comprises the pharmaceutical composition comprising of 120 mg or 150 mg of the compound of formula (I) or the pharmaceutically acceptable salt thereof in multiple doses, wherein the content of the compound of formula (I) or the pharmaceutically acceptable salt thereof is a once-daily dose; the multiple doses consist of single doses, wherein the single dose is the pharmaceutical composition of 30 mg or 60 mg of the compound of formula (I) or the pharmaceutically acceptable salt thereof.

The compound of formula (I) of the present disclosure can be administered in its free base form, or in the form of its pharmaceutically acceptable salt, hydrate or prodrug that converts in vivo into the free base form of the compound of formula (I). For example, pharmaceutically acceptable salts of the compound of formula (I) within the scope of the present disclosure may be produced from various organic acids and inorganic acids according to methods well known in the art; for example, the inorganic acids may be selected from the group consisting of hydrochloric acid, hydrobromic acid, sulfuric acid, nitric acid and phosphoric acid, and the organic acids may be selected from the group consisting of succinic acid, maleic acid, acetic acid, fumaric acid, citric acid, tartaric acid, benzoic acid, p-toluenesulfonic acid, methanesulfonic acid and naphthalenesulfonic acid. In some embodiments of the present disclosure, the compound of formula (I) is administered in its free base form.

The "compound of formula (I)" described in the present disclosure may be a "pharmaceutical composition of the compound of formula (I)".

The "compound of formula (I) or the pharmaceutically acceptable salt thereof" described in the present disclosure may be a "pharmaceutical composition of the compound of formula (I) or the pharmaceutically acceptable salt thereof".

The dosage regimen can be determined comprehensively depending on the activity and toxicity of the medicament, tolerance of a patient, etc.

In some embodiments, the pharmaceutical composition of the compound of formula (I) or the pharmaceutically acceptable salt thereof disclosed herein further comprises a pharmaceutically acceptable excipient.

In some embodiments, the pharmaceutical composition of the compound of formula (I) or the pharmaceutically acceptable salt thereof disclosed herein is administered orally.

In some embodiments, the pharmaceutical composition of the compound of formula (I) or the pharmaceutically acceptable salt thereof disclosed herein is a solid pharmaceutical composition.

In some embodiments, the solid pharmaceutical composition of the compound of formula (I) or the pharmaceutically acceptable salt thereof disclosed herein is formulated in the form of a capsule.

In some embodiments, the pharmaceutical composition of the compound of formula (I) or the pharmaceutically acceptable salt thereof is a capsule of the compound of formula (I) or the pharmaceutically acceptable salt thereof with a strength of 30 mg and 60 mg.

The pharmaceutical composition of the compound of formula (I) or the pharmaceutically acceptable salt thereof disclosed herein can be manufactured using methods well known in the art, such as conventional mixing, dissolving, granulating, dragee-making, levigating, emulsifying, and lyophilizing.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

In some embodiments, the pharmaceutical composition of the compound of formula (I) may be a capsule of the compound of formula (I) comprising the compound of formula (I), corn starch, carboxymethylcellulose calcium, hydroxypropyl methylcellulose and magnesium stearate.

In other embodiments, the pharmaceutical composition of the compound of formula (I) may be a capsule of the compound of formula (I) comprising the compound of formula (I), lactose, microcrystalline cellulose, sodium carboxymethyl starch and magnesium stearate.

In one specific embodiment of the present disclosure, the pharmaceutical composition of the compound of formula (I) is a capsule of the compound of formula (I) comprising: (a) about 30 mg or about 60 mg of the compound of formula (I), (b) about 93 mg or about 63 mg of corn starch, (c) about 22.5 mg of carboxymethylcellulose calcium, (d) about 3 mg of hydroxypropyl methylcellulose, and (e) about 1.5 mg of magnesium stearate, with a total weight of 150 mg.

In one specific embodiment of the present disclosure, the pharmaceutical composition of the compound of formula (I) is a capsule of the compound of formula (I), comprising: (a) about 30 mg or about 60 mg of the compound of formula (I), (b) about 40 mg of lactose, (c) about 72.5 mg or about 42.5 mg of microcrystalline cellulose, (d) about 6 mg of sodium carboxymethyl starch, and (e) about 1.5 mg of magnesium stearate, with a total weight of 150 mg.

In another aspect, the present disclosure also provides a kit of pharmaceutical compositions for use in treating cancer, which comprises (a) a first pharmaceutical composition comprising the anti-PD-L1 antibody disclosed herein as an active ingredient; and (b) a second pharmaceutical composition comprising a compound of formula (I) or a pharmaceutically acceptable salt thereof as an active ingredient.

In another aspect, the present disclosure further provides a method for treating cancer, which comprises administering to an entity suffering from cancer a therapeutically effective amount of the combined pharmaceutical composition disclosed herein.

In another aspect, the present disclosure further provides use of a combined pharmaceutical composition for preparing a medicament for use in treating cancer, and the combined pharmaceutical composition is the combined pharmaceutical composition disclosed herein.

In another aspect, the present disclosure further provides use of a combined pharmaceutical composition for treating cancer, and the combined pharmaceutical composition is the combined pharmaceutical composition disclosed herein.

In another aspect, the present disclosure further provides a combination treatment method for treating an entity suffering from cancer, which comprises administering to the entity a therapeutically effective amount of a compound of formula (I) or a pharmaceutically acceptable salt thereof alone, and a therapeutically effective amount of the anti-PD-L1 antibody disclosed herein alone.

In some specific embodiments, the cancer is selected from the group consisting of liver cancer and gastric cancer.

In some specific embodiments, the liver cancer is hepatocellular carcinoma and the gastric cancer is gastric adenocarcinoma or gastroesophageal junction adenocarcinoma.

In some embodiments of the combined pharmaceutical composition, or in some embodiments of the method, use or combination treatment method, the anti-PD-L1 antibody is continuously administered at a dose of 1 mg/kg, 2 mg/kg, 3 mg/kg, 5 mg/kg, 6 mg/kg, 9 mg/kg, 10 mg/kg, 15 mg/kg, 20 mg/kg or 30 mg/kg body weight. In some embodiments, the anti-PD-L1 antibody is administered at one or more flat doses that can effectively treat the cancer. In some specific embodiments, the flat dose is in the range of about 20 mg to about 2400 mg, about 600 mg to about 2400 mg, or about 1000 mg to about 1500 mg of the anti-PD-L1 antibody. In some specific embodiments, the flat dose is selected from the group consisting of about 100 mg, about 300 mg, about 600 mg, about 900 mg, about 1000 mg, about 1200 mg, about 1500 mg, about 1800 mg, about 2100 mg and about 2400 mg of the anti-PD-L1 antibody. In some specific embodiments, the flat dose is selected from about 1200 mg of the anti-PD-L1 antibody.

In some embodiments of the combined pharmaceutical composition, or in some embodiments of the method, use or combination treatment method, the anti-PD-L1 antibody can be administered at a flat dose (the dose administered to a patient regardless of the patient's body weight). For example, the flat dose of 13C5, ch13C5-hIgG1, ch13C5-hIgG4, hu13C5-hIgG1, hu13C5-hIgG4, 5G11, ch5G11-hIgG1, ch5G11-hIgG4, hu5G11-hIgG1 or hu5G11-hIgG4 mAb may be about 1200 mg. In certain embodiments, the anti-PD-L1 antibody is administered at a dose of about 1200 mg. In certain embodiments, the anti-PD-L1 antibody is administered at a dose of about 900 mg. In certain embodiments, the anti-PD-L1 antibody is administered at a dose of about 600 mg. In one embodiment, 900 mg of the anti-PD-L1 antibody is administered once every 3 weeks. In another embodiment, 1200 mg of the anti-PD-L1 antibody is administered once every 3 weeks.

In some embodiments of the combined pharmaceutical composition, or in some embodiments of the method, use or combination treatment method, the anti-PD-L1 antibody is administered about every week (q1w), about every 2 weeks (q1w), about every 3 weeks (q1w) or about every 4 weeks (q1w). In some specific embodiments, the patient is administered a flat dose of the anti-PD-L1 antibody about every 3 weeks (21 days). In some specific embodiments, the anti-PD-L1 antibody is continuously administered at a dose of 1200 mg per patient once about every 3 weeks (21 days).

In some embodiments of the combined pharmaceutical composition, or in some embodiments of the method, use or combination treatment method, the anti-PD-L1 antibody is administered by intravenous infusion. In some specific embodiments, the anti-PD-L1 antibody is administered by intravenous infusion over about 1-2 h, preferably by intravenous infusion over about 1 h (±5 min).

In some embodiments of the combined pharmaceutical composition, or in some embodiments of the method, use or combination treatment method, the anti-PD-L1 antibody is hu5G11-hIgG1 injection, and the package strength of the hu5G11-hIgG1 injection is 100 mg:10 mL or 600 mg:20 mL; the administration regimen is a single intravenous infusion of 1200 mg of hu5G11-hIgG1 (diluted to 250 mL with normal saline), and the infusion time is 60±5 min. The administration is carried out once every 21 days.

In some embodiments of the combined pharmaceutical composition, or in some embodiments of the method, use or combination treatment method, the content of the compound of formula (I) or the pharmaceutically acceptable salt thereof in the combined pharmaceutical composition is a daily dose, which is administered as follows: the compound of formula (I) or the pharmaceutically acceptable salt thereof is administered once daily.

In some embodiments of the combined pharmaceutical composition, or in some embodiments of the method, use or combination treatment method, the content of the compound of formula (I) or the pharmaceutically acceptable salt thereof in the combined pharmaceutical composition is a daily dose, which is administered as follows: the compound of formula (I) or the pharmaceutically acceptable salt thereof is administered once daily over 21 consecutive days.

In some embodiments of the combined pharmaceutical composition, or in some embodiments of the method, use or combination treatment method, the content of the compound of formula (I) or the pharmaceutically acceptable salt thereof in the combined pharmaceutical composition is a daily dose, wherein the compound of formula (I) or the pharmaceutically acceptable salt thereof is administered in a single dose or in multiple doses. In some embodiments, the compound of formula (I) or the pharmaceutically acceptable salt thereof is administered in multiple doses.

In some embodiments of the combined pharmaceutical composition, or in some embodiments of the method, use or combination treatment method, the compound of formula (I) or the pharmaceutically acceptable salt thereof is administered as follows: continuously administering daily to a subject a daily dose of 90 mg, 120 mg, 150 mg or 180 mg of the compound of formula (I) or the pharmaceutically acceptable salt thereof.

In some embodiments of the combined pharmaceutical composition, or in some embodiments of the method, use or combination treatment method, the compound of formula (I) or the pharmaceutically acceptable salt thereof is administered as follows: at a daily dose of 90 mg, 120 mg, 150 mg or 180 mg once daily, with 21 days as a treatment cycle.

In some embodiments of the combined pharmaceutical composition, or in some embodiments of the method, use or combination treatment method, the compound of formula (I) or the pharmaceutically acceptable salt thereof is administered orally; in some embodiments, the compound of formula (I) or the pharmaceutically acceptable salt thereof is administered orally within +5 min of administration of the pharmaceutical composition of the anti-PD-L1 antibody.

In some embodiments of the combined pharmaceutical composition, or in some embodiments of the method, use or combination treatment method, the compound of formula (I) or the pharmaceutically acceptable salt thereof is administered at a fixed time every day.

In some embodiments of the combined pharmaceutical composition, or in some embodiments of the method, use or combination treatment method, the administration is carried out as follows: administering the compound of formula (I) or the pharmaceutically acceptable salt thereof within +5 min of administration of the anti-PD-L1 antibody.

In some embodiments of the combined pharmaceutical composition, or in some embodiments of the method, use or combination treatment method, the administration is carried out as follows: administering the pharmaceutical composition of the compound of formula (I) or the pharmaceutically acceptable salt thereof within +5 min of administration of the pharmaceutical composition of the anti-PD-L1 antibody.

In some embodiments of the combined pharmaceutical composition, or in some embodiments of the method, use or combination treatment method, the administration is carried out as follows: administering a capsule of the compound of formula (I) or the pharmaceutically acceptable salt thereof on an empty stomach within +5 min of administration of the anti-PD-L1 antibody injection.

In some embodiments of the combined pharmaceutical composition, or in some embodiments of the method, use or combination treatment method, the administration is carried out as follows: administering the compound of formula (I) or the pharmaceutically acceptable salt thereof in combination with the anti-PD-L1 antibody in 21-day treatment cycles, and the administration is done by administering by infusion 1200 mg of the anti-PD-L1 antibody over a period of 60±5 min on the first day, and administering 120 mg or 150 mg of the compound of formula (I) or the pharmaceutically acceptable salt thereof once daily over 21 consecutive days.

In some embodiments of the combined pharmaceutical composition, or in some embodiments of the method, use or combination treatment method, the administration is carried out as follows: administering the compound of formula (I) or the pharmaceutically acceptable salt thereof in combination with the hu5G11-hIgG1 antibody in 21-day treatment cycles, and the administration is done by administering by infusion 1200 mg of the hu5G11-hIgG1 antibody over a period of 60±5 min on the first day, and administering 120 mg of the compound of formula (I) or the pharmaceutically acceptable salt thereof once daily over 21 consecutive days.

In some embodiments of the combined pharmaceutical composition, or in some embodiments of the method, use or combination treatment method, the administration is carried out as follows: administering the compound of formula (I) or the pharmaceutically acceptable salt thereof in combination with the hu5G11-hIgG1 antibody in 21-day treatment cycles, and the administration is done by administering by infusion 1200 mg of the hu5G11-hIgG1 antibody over a period of 60±5 min on the first day, and administering 150 mg of the compound of formula (I) or the pharmaceutically acceptable salt thereof once daily over 21 consecutive days.

In some embodiments of the combined pharmaceutical composition, or in some embodiments of the method, use or combination treatment method, 1200 mg of the hu5G11-hIgG1 antibody is diluted to 250 mL with normal saline before administration. In some embodiments of the present disclosure, the compound of formula (I) or the pharmaceutically acceptable salt thereof is administered on the first day within ±5 min of starting infusion of hu5G11-hIgG1 antibody on an empty stomach.

In some embodiments of the present disclosure, the cancer is gastric cancer.

In some embodiments of the present disclosure, the gastric cancer is advanced and/or metastatic gastric cancer.

In some embodiments of the present disclosure, the gastric cancer is recurrent gastric cancer.

In some embodiments of the present disclosure, the gastric cancer is advanced and/or metastatic gastric cancer that has failed treatment with a taxane anti-tumor drug, a camptothecin analog anti-tumor drug, an adriamycin anti-tumor drug, a platinum complex and/or a fluoropyrimidine derivative.

In some embodiments of the present disclosure, the gastric cancer is moderately or poorly differentiated gastric cancer.

In some embodiments of the present disclosure, the gastric cancer is unresectable gastric cancer.

In some embodiments of the present disclosure, the gastric cancer is gastric cancer that has progressed after surgical treatment. In some embodiments of the present disclosure, the gastric cancer is gastric cancer that has failed chemotherapy. In some embodiments of the present disclosure, the gastric cancer is gastric cancer that has failed first-line standard chemotherapy.

In some embodiments of the present disclosure, the gastric cancer is advanced gastric cancer that is not suitable for surgery or has progressed after surgical treatment and has failed first-line standard chemotherapy. In some embodiments of the present disclosure, the gastric cancer is advanced gastric cancer that is not suitable for surgery and has failed first-line standard chemotherapy. In some embodiments of the present disclosure, the gastric cancer is advanced gastric cancer that is not suitable for surgery and has failed first-line standard chemotherapy (no less than 2 cycles of treatment).

In some embodiments of the present disclosure, the disease progresses during the first-line treatment of the gastric cancer, or within 4 months after the end of treatment after the last administration (maintenance monotherapy including first-line treatment). In some embodiments of the present disclosure, the gastric cancer has a recurrence or metastasis during neoadjuvant or adjuvant therapy or within 6 months after the last administration.

In some embodiments of the present disclosure, the gastric cancer is gastric adenocarcinoma.

In some embodiments of the present disclosure, the gastric adenocarcinoma is recurrent gastric adenocarcinoma.

In some embodiments of the present disclosure, the gastric cancer is gastric cancer (e.g., gastric adenocarcinoma) with pTNM stage of pT3N3.

In some embodiments of the present disclosure, the gastric adenocarcinoma is advanced and/or metastatic gastric adenocarcinoma that has failed treatment with a taxane anti-tumor drug, a camptothecin analog anti-tumor drug, an adriamycin anti-tumor drug, a platinum complex and/or a fluoropyrimidine derivative.

In some embodiments of the present disclosure, the gastric cancer is gastric cancer (e.g., gastric adenocarcinoma) that has been previously treated (e.g., has failed treatment) with oxaliplatin in combination with capecitabine.

In some embodiments of the present disclosure, the gastric cancer is gastric cancer (e.g., gastric adenocarcinoma) that has been previously treated (e.g., has failed treatment) with oxaliplatin.

In some embodiments of the present disclosure, the gastric cancer is gastric cancer (e.g., gastric adenocarcinoma) that has been previously treated (e.g., has failed treatment) with oxaliplatin in combination with capecitabine, followed by maintenance therapy with oxaliplatin.

In some embodiments of the present disclosure, the gastric cancer is gastric cancer (e.g., gastric adenocarcinoma) that has been previously treated (e.g., has failed treatment) with docetaxel and oxaliplatin in combination with tegafur-gimeracil-oteracil potassium.

In some embodiments of the present disclosure, the gastric cancer is gastric cancer (e.g., gastric adenocarcinoma) that has been previously treated (e.g., has failed treatment) with tegafur-gimeracil-oteracil potassium.

In some embodiments of the present disclosure, the gastric cancer is gastric cancer (e.g., gastric adenocarcinoma) that has been previously treated (e.g., has failed treatment) with docetaxel and oxaliplatin in combination with tegafur-gimeracil-oteracil potassium, followed by maintenance therapy with oxaliplatin.

In some embodiments of the present disclosure, the gastric adenocarcinoma is unresectable gastric adenocarcinoma.

In some embodiments of the present disclosure, the gastric adenocarcinoma is gastric adenocarcinoma that has progressed after surgical treatment.

In some embodiments of the present disclosure, the gastric adenocarcinoma is gastric adenocarcinoma that has failed chemotherapy. In other embodiments, the failure of chemotherapy includes failure of a platinum-containing chemotherapy regimen, failure of a fluorouracil-containing chemotherapy regimen, failure of systemic standard chemotherapy, or failure of first-line or more lines of standard chemotherapy. In some embodiments of the present disclosure, the gastric adenocarcinoma is gastric adenocarcinoma that has failed first-line standard chemotherapy.

In some embodiments of the present disclosure, the gastric adenocarcinoma is advanced gastric adenocarcinoma that is not suitable for surgery or has progressed after surgical treatment and has failed first-line standard chemotherapy. In some embodiments of the present disclosure, the gastric adenocarcinoma is advanced gastric adenocarcinoma that is not suitable for surgery and has failed first-line standard chemotherapy.

In some embodiments of the present disclosure, the gastric adenocarcinoma gatric cancer is advanced gastric adenocarcinoma that is not suitable for surgery and has failed first-line standard chemotherapy (no less than 2 cycles of treatment). In some embodiments of the present disclosure, the gastric adenocarcinoma is advanced gastric adenocarcinoma that is not suitable for surgery or has progressed after surgical treatment and has failed first-line standard chemotherapy (must include no less than 2 cycles of platinum and fluorouracil treatment).

In some embodiments of the present disclosure, the disease progresses during the first-line treatment of the gastric adenocarcinoma, or within 4 months after the end of treatment after the last administration (maintenance monotherapy including first-line treatment). In some embodiments of the present disclosure, the gastric adenocarcinoma has a recurrence or metastasis during neoadjuvant or adjuvant therapy or within 6 months after the last administration.

In some embodiments of the present disclosure, the gastric cancer is gastroesophageal junction adenocarcinoma.

In some embodiments of the present disclosure, the gastroesophageal junction adenocarcinoma is recurrent gastroesophageal junction adenocarcinoma.

In some embodiments of the present disclosure, the gastroesophageal junction adenocarcinoma is advanced and/or metastatic gastroesophageal junction adenocarcinoma that has failed treatment with a taxane anti-tumor drug, a camptothecin analog anti-tumor drug, an adriamycin anti-tumor drug, a platinum complex and/or a fluoropyrimidine derivative.

In some embodiments of the present disclosure, the gastroesophageal junction adenocarcinoma is unresectable gastroesophageal junction adenocarcinoma.

In some embodiments of the present disclosure, the gastroesophageal junction adenocarcinoma is gastroesophageal junction adenocarcinoma that has progressed after surgical treatment.

In some embodiments of the present disclosure, the gastroesophageal junction adenocarcinoma is gastroesophageal junction adenocarcinoma that has failed chemotherapy. In other embodiments, the failure of chemotherapy includes failure of a platinum-containing chemotherapy regimen, failure of a fluorouracil-containing chemotherapy regimen, failure of systemic standard chemotherapy, or failure of first-line or more lines of standard chemotherapy. In some embodiments of the present disclosure, the gastroesophageal junction adenocarcinoma is gastroesophageal junction adenocarcinoma that has failed first-line standard chemotherapy.

In some embodiments of the present disclosure, the gastroesophageal junction adenocarcinoma is advanced gastroesophageal junction adenocarcinoma that is not suitable for surgery and has failed first-line standard chemotherapy.

In some embodiments of the present disclosure, the gastroesophageal junction adenocarcinoma is advanced gastroesophageal junction adenocarcinoma that is not suitable for surgery and has failed first-line standard chemotherapy (no less than 2 cycles of treatment).

In some embodiments of the present disclosure, the disease progresses during the first-line treatment of the gastroesophageal junction adenocarcinoma, or within 4 months after the end of treatment after the last administration (maintenance monotherapy including first-line treatment). In some embodiments of the present disclosure, the gastroesophageal junction adenocarcinoma has a recurrence or metastasis during neoadjuvant or adjuvant therapy or within 6 months after the last administration.

In some embodiments of the present disclosure, the gastric cancer is gastric adenocarcinoma that has been previously treated with oxaliplatin in combination with capecitabine after radical surgery (e.g. 8 cycles), followed by maintenance therapy with oxaliplatin.

In some embodiments of the present disclosure, the gastric cancer is gastric adenocarcinoma that has been previously treated with docetaxel and oxaliplatin in combination with tegafur-gimeracil-oteracil potassium (e.g., 8 cycles), followed by maintenance therapy with tegafur-gimeracil-oteracil potassium.

In some embodiments of the present disclosure, the cancer is liver cancer.

In some embodiments of the present disclosure, the liver cancer is moderately or poorly differentiated liver cancer.

In some embodiments of the present disclosure, the liver cancer is hepatocellular carcinoma.

In some embodiments of the present disclosure, the liver cancer is liver parenchymal cell cancer.

In some embodiments of the present disclosure, the liver cancer is advanced hepatocellular carcinoma.

In some embodiments of the present disclosure, the liver cancer is liver cancer that has not been treated systemically.

In some embodiments of the present disclosure, the liver cancer is liver cancer that has not been treated with any systemic treatment for HCC.

In some embodiments of the present disclosure, the liver cancer is liver cancer (e.g., hepatocellular carcinoma) that has not previously been treated with surgical treatment, chemotherapy, radiotherapy, or anti-tumor drug therapy.

In some embodiments of the present disclosure, the liver cancer is liver cancer that is not suitable for local treatment or is refractory to local treatment.

In some embodiments of the present disclosure, the liver cancer is liver cancer that is not suitable for local treatment or is refractory to local treatment, and is not suitable for treatment with radical therapy.

In some embodiments of the present disclosure, the liver cancer is liver cancer with TNM stage of T3bN0M0.

In some embodiments of the present disclosure, the liver cancer is liver cancer with clinical stage IIIB.

In some embodiments of the present disclosure, the liver cancer is liver cancer with Barcelona clinic liver cancer stage (BCLC stage) B or C, which is not suitable for surgery or local treatment, or has progressed after surgery or local treatment.

In some embodiments of the present disclosure, the liver cancer is liver cancer with Barcelona clinic liver cancer stage (BCLC stage) B.

In some embodiments of the present disclosure, the liver cancer is liver cancer with Barcelona clinic liver cancer stage (BCLC stage) C, or liver cancer with stage B that is not suitable for local treatment or is refractory to local treatment, and is not suitable for treatment with radical therapy.

In some embodiments of the present disclosure, the local treatment includes, but is not limited to, surgery, TACE, TAI, radiofrequency or microwave ablation, or absolute alcohol injection.

In some embodiments of the present disclosure, the liver cancer is liver cancer with Child-Pugh liver function grade A.

In some embodiments of the present disclosure, the criteria for patients with the liver cancer are as follows: patients who progress after local treatment (including but not limited to surgery, TACE, radiofrequency or microwave ablation, absolute alcohol injection) should be at least 4 weeks after the end of local treatment and elicit a toxic response rated $\leq 1$ by National Cancer Institute Common Terminology Criteria for Adverse Events, version 5.0 (NCI-CTCAE 5.0).

In some embodiments of the present disclosure, the criteria for patients with the liver cancer are as follows: patients after local treatment (including but not limited to surgery, TACE, TAI, radiofrequency or microwave ablation, absolute alcohol injection) should be at least 4 weeks after the end of local treatment and have recovered sufficiently from treatment toxicity and/or complications.

In some embodiments of the present disclosure, the liver cancer is advanced hepatocellular carcinoma that has not been treated systemically.

In some embodiments of the present disclosure, the liver cancer is recurrent liver cancer.

In some embodiments of the present disclosure, the liver cancer is unresectable liver cancer.

In some embodiments of the present disclosure, the liver cancer is liver cancer that has failed chemotherapy. In other embodiments, the failure of chemotherapy includes failure of a platinum-containing chemotherapy regimen, failure of systemic standard chemotherapy, or failure of first-line or more lines of chemotherapy (e.g. standard chemotherapy).

In some embodiments of the present disclosure, the liver cancer is metastatic liver cancer. In other embodiments, the metastatic liver cancer is a metastatic cancer metastasizing from lung cancer, gastric cancer, rectal cancer, colon cancer, colorectal cancer, pancreatic cancer, or breast cancer.

Technical Effects

The combined pharmaceutical composition disclosed herein has one or more of the following effects:

(1) better efficacy in controlling tumor growth or even eliminating tumors as compared with either drug of the combination administered alone;

(2) fewer doses as compared with either drug of the combination administered alone;

(3) good tolerability in patients, and fewer adverse effects and/or complications as compared with either drug administered alone;

(4) a higher disease control rate in patients treated;

(5) longer survivals (e.g., median survival, progression-free survival, or overall survival) in patients treated; (6) longer survivals (e.g., median survival, progression-free survival, or overall survival) in patients treated as compared with standard chemotherapies;

(7) a longer duration of response (DOR); and/or (8) better activity in treating tumors or proliferative diseases and better anti-tumor synergistic effect, as compared with either drug of the combination administered alone.

Definitions and Description

Unless otherwise stated, the following terms used in the present disclosure shall have the following meanings. A certain term, unless otherwise specifically defined, should not be considered uncertain or unclear, but construed according to its common meaning in the field. When referring to a trade name, it is intended to refer to its corresponding commercial product, composition or its active ingredient.

The word "comprise" and variations thereof such as "comprises" or "comprising" will be understood in an open, non-exclusive sense, i.e., "including but not limited to".

As used herein, the term "antibody" refers to an antigen-binding protein having at least one antigen-binding domain. The antibody and the fragment thereof of the present disclosure can be an intact antibody or any fragment thereof. Thus, the antibody and the fragment thereof of the present disclosure include a monoclonal antibody or a fragment thereof and an antibody variant or a fragment thereof, as well as an immunoconjugate. Examples of the antibody fragment include a Fab fragment, a Fab' fragment, a F(ab)'2 fragment, a Fv fragment, an isolated CDR region, a single chain Fv molecule (scFv), and other antibody fragments known in the art. The antibody and the fragment thereof may also include a recombinant polypeptide, a fusion protein, and a bispecific antibody. The anti-PD-L1 antibody and the fragment thereof disclosed herein can be of IgG1, IgG2, IgG3, or IgG4 isotype. The term "isotype" refers to the class of antibodies encoded by the heavy chain constant region gene.

The term "treatment" usually refers to operations for acquiring needed pharmacological effect and/or physiological effect. In terms of fully or partially preventing a disease or a symptom thereof, the effect can be preventive; and/or in terms of partially or fully stabilizing or curing the disease and/or a side effect of the disease, the effect can be therapeutic. As used herein, "treat", "treating" and "treatment" encompass any treatment of a disease in a patient, including (a) inhibiting a symptom of the disease, i.e., blocking the progression of the disease; or (b) alleviating a symptom of the disease, i.e., causing remission of the disease or the symptom.

As used herein, the term "general treatment" refers to treatment in which a drug substance is transported through the bloodstream to reach and affect cells of the whole body.

As used herein, the term "systemic treatment" refers to systemic chemotherapy, and systemic or local radiotherapy.

As used herein, the term "first-line treatment" refers to treatment with drugs that are the first or standard choice according to patient's conditions.

"Administering" means physically introducing the composition comprising the therapeutic agent to the entity using any of a variety of methods and delivery systems known to those skilled in the art. Routes of administration include intravenous, intramuscular, subcutaneous, intraperitoneal, spinal or other parenteral routes, for example by injection or infusion. As used herein, the phrase "parenteral administration" refers to modes of administration apart from enteral and local administration, typically by injection, including but not limited to, intravenous, intramuscular, intra-arterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion and in vivo electroporation. In certain embodiments, the administration is carried out via a non-parenteral route, and in certain embodiments, via oral administration. Other non-parenteral routes include local, epidermal or mucosal routes, for example, intranasal, vaginal, rectal, sublingual or local routes. Administration may also be performed, e.g., once, multiple times, and/or over one or more extended periods of time.

As used herein, an "adverse event" (AE) is any adverse and often unintended or undesirable sign (including abnormal laboratory findings), symptom, or disease associated with the use of medical therapy. For example, an adverse event may be associated with activation of the immune system or expansion of immune system cells (e.g., T cells) in response to treatment. The medical treatment may have one or more related AEs, and each AE may have the same or a different severity level. Reference to a method capable of "altering an adverse event" refers to a treatment regimen that reduces the incidence and/or severity of one or more AEs associated with the use of a different treatment regimen.

As used herein, "administration interval" refers to the amount of time that elapses among multiple doses of a formulation disclosed herein administered to an entity. The administration interval may thus be indicated as a range.

As used herein, the term "administration frequency" refers to the frequency at which doses of a formulation disclosed herein are administered over a given time. The administration frequency may be indicated as the number of administrations per given time, e.g., once every week or once every 2 weeks.

The term "flat dose" refers to a dose administered to a patient without considering the weight or the body surface area (BSA) of the patient. Thus, the flat dose is specified as the absolute amount of a medicament (e.g., anti-PD-L1 antibody) rather than the mg/kg dose. For example, a 60 kg human and a 100 kg human will receive the same dose of antibody (e.g., 240 mg of anti-PD-L1 antibody).

The term "fixed dose" in reference to a composition of the present disclosure means that two or more different antibodies in a single composition are present in the composition in a specific (fixed) ratio to each other. In some embodiments, the fixed dose is based on the weight of the antibody (e.g., mg). In some embodiments, the fixed dose is based on the concentration of the antibody (e.g., mg/mL).

"Body weight-based dose" as used herein refers to a dose calculated based on the weight of a patient and administered to the patient. For example, when a patient weighing 60 kg requires 3 mg/kg of anti-PD-L1 antibody and 1 mg/kg of anti-CTLA-4 antibody, one can extract appropriate amounts of anti-PD-L1 antibody (i.e., 180 mg) and anti-CTLA-4 antibody (i.e., 60 mg) at a time from a 3:1 fixed-dose formulation of anti-PD-L1 antibody and anti-CTLA-4 antibody.

The term "daily dose" refers to a dose administered to a patient per day.

The term "single dose" refers to the smallest unit of packaging containing a certain amount of pharmaceutical product; for example, in a box of seven capsules, each capsule is a single dose; in a box of seven tablets, each tablet is a single dose; or a vial of injection is a single dose.

The term "multiple dose" consists of multiple single doses.

The terms "day", "daily", etc., when referred to in an administration regimen, refer to the time within a calendar day that starts at midnight and ends at the next midnight.

The term "immunotherapy" refers to the treatment of an entity with a disease or at risk of infection or relapse of a disease by a method that comprises inducing, enhancing, suppressing or otherwise altering an immune response.

The "treatment" or "therapy" for an entity refers to any type of intervention or procedure performed on the entity or the administration of an active agent to the entity, for the purpose of reversing, alleviating, ameliorating, inhibiting, slowing or preventing the onset, progression, development, severity or recurrence of a symptom, complication, or condition, or biochemical indicators associated with the disease.

"Programmed death ligand-1 (PD-L1)" is one of two cell surface glycoprotein ligands for PD-1 (the other is PD-L2), which down-regulates T cell activation and cytokine secretion upon binding to PD-1.

"Entity" includes any human or non-human animal. The term "non-human animal" includes, but is not limited to, vertebrates such as non-human primates, sheep, dogs, and rodents such as mice, rats and guinea pigs. In certain embodiments, the entity is a human. "Subject" refers to a mammal, such as a rodent, feline, canine, and primate. Preferably, the subject according to the present disclosure is a human. The terms "entity", "subject" and "patient" are used interchangeably herein in certain contexts.

A "therapeutically effective amount" or "therapeutically effective dose" of a drug or therapeutic agent is any amount of a drug that, when used alone or in combination with another therapeutic agent, protects an entity from the onset of a disease or promotes disease regression as evidenced by reduction in the severity of disease symptoms, increase in the frequency and duration of disease symptom-free stage, or the prevention of damage or disability caused by the affliction of the disease. The ability of a therapeutic agent to promote disease regression can be evaluated using a variety of methods known to skilled practitioners, such as in a human entity during clinical trials, in an animal model system that predicts efficacy for humans, or by determining the activity of the drug in an in vitro assay.

As an example for treating a tumor, a therapeutically effective amount of an anti-cancer drug can inhibit cell growth or tumor growth by at least about 10%, at least about 20%, at least about 40%, at least about 60%, or at least about 80% relative to an untreated entity, or, in certain embodiments, relative to a patient treated with standard of care therapy. In other embodiments of the present disclosure, tumor regression may be observed for a period of at least about 20 days, at least about 40 days, or at least about 60 days. Despite these final measurements of therapeutic effectiveness, the evaluation of immunotherapeutic drugs must also take into account "immune-related" response patterns.

In the present disclosure, "cancer" refers to a wide variety of diseases characterized by the uncontrolled growth of abnormal cells in the body. "Cancer" or "cancer tissue" may include a tumor. Unregulated cell division and growth lead to the formation of malignant tumors that invade adjacent tissues and may also metastasize to distant parts of the body through the lymphatic system or the blood flow.

A "recurrent" cancer is one that regenerates at the initial site or a distant site after being responsive to initial treatment (e.g., surgery). A "locally recurrent" cancer is one that occurs, after treatment, at the same location as the previously treated cancer.

An "unresectable" cancer is one that cannot be removed by surgery.

A "metastatic" cancer refers to one that spreads from one part of the body (e.g., the lung) to another part of the body.

"Failure of a platinum-containing chemotherapy regimen" refers to the disease progression or intolerance to toxic and side effects during or after first-line chemotherapy or radiotherapy and chemotherapy with a platinum-containing regimen.

"Failure of a fluorouracil-containing chemotherapy regimen" refers to the disease progression or intolerance to toxic and side effects during or after first-line chemotherapy or radiotherapy and chemotherapy with a fluorouracil-containing regimen.

"Failure of systemic standard chemotherapy" is defined as: the disease progression during the treatment or after the last treatment; or intolerance to toxic and side effects during the treatment.

"Failure of first-line or more lines of chemotherapy" is defined as: the disease progression during the treatment or after the last treatment; or intolerance to toxic and side effects during the treatment.

The use of alternatives (e.g., "or") shall be understood to refer to any one, two, or any combination of the alternatives. Although the disclosure supports the definition of the term "or" as merely an alternative and "and/or", the term "or" in the claims means "and/or" unless it is explicitly stated to be only an alternative or mutually exclusive between alternatives.

As used herein, the indefinite article "a" or "an" shall be understood to mean "one or more" of any listed or enumerated components. In the claims and/or the specification of the present disclosure, unless otherwise stated in the context, an indication such as "a/an", "said" or "the" is intended to support both the singular and/or plural cases. The terms "about", "approximately" or "substantially comprise" refers to a value or composition within an acceptable error range for the particular value or composition as determined by one of ordinary skill in the art, which will depend in part on how the value or composition is measured or determined, i.e., the limitations of the measurement system. For example, "about", "approximately" or "substantially comprise" may refer to being within 1 or more than 1 standard deviation as practiced in the art. Alternatively, "about" or "substantially comprises" may refer to a range that differs by up to 10% or 20% (i.e., ±10% or ±20%) from the parameter or value modified thereby. For example, about 3 mg may include any number between 2.7 mg and 3.3 mg (for 10%) or between 2.4 mg and 3.6 mg (for 20%). Furthermore, particularly with respect to biological systems or processes, the term may refer to being up to an order of magnitude or up to at most 5 times the numerical value. When a particular value or composition is provided in the present disclosure and claims, unless otherwise stated, the meaning of "about" or "substantially comprise" should be assumed to be within an acceptable error range of the particular value or composition.

As used herein, the term "about once every week", "about once every two weeks" or any other similar administration interval term refers to an approximation. "About once every week" may include once every 7±1 days, i.e., once every 6 days to once every 8 days. "About once every two weeks" may include once every 14±3 days, i.e., once every 11 days to once every 17 days. Similar approximations apply to, for example, about once every 3 weeks, about once every 4 weeks, about once every 5 weeks, about once every 6 weeks, and about once every 12 weeks. In certain embodiments, an administration interval of about once every 6 weeks or about once every 12 weeks means that a first dose may be administered on any day of the first week, and then a second dose may be administered on any day of the sixth or twelfth week, respectively. In other embodiments, an administration interval of about once every 6 weeks or about once every 12 weeks means that a first dose is administered on a particular day (e.g., Monday) of the first week and then a second dose is administered on the same day (i.e., Monday) of the sixth or twelfth week, respectively. Similar principles apply to phrases including but not limited to, "about once every 2 weeks", "about once every month", etc.

As used herein, unless otherwise indicated, any concentration range, percentage range, ratio range, or integer range shall be understood as including the value of any integer within the listed range and including, when appropriate, fractions thereof (such as one tenth and one hundredth of the integer).

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "fixed combination" refers to administration of the active components (for example, the anti-PD-L1 antibody or the compound of formula (I)) to a subject simultaneously at a fixed total dose or in a fixed dose proportion, or in the form of a single substance, pharmaceutical composition or formulation.

The term "non-fixed combination" refers to simultaneous, parallel, or sequential and temporally unlimited administration of two or more aforementioned active components as independent substances (for example, a pharmaceutical composition and a formulation) to a subject, wherein the active ingredients administered to the subject reach therapeutically effective amounts. An example, which can be listed, of the non-fixed combination is a cocktail therapy, for example, 3 or more active components are administered. In a non-fixed combination, each active ingredient can be packaged, sold or administered as a fully independent pharmaceutical composition. The term "non-fixed combination" also includes combined use of "fixed combinations", or a "fixed combination" and an independent substance of any one or more active components.

As used herein, "combined use" or "use in combination" means that two or more active substances may be administered to a subject as a mixture, simultaneously as a single formulation, or sequentially in any order as a single formulation.

The term "pharmaceutical composition" refers to a mixture consisting of one or more of the active ingredients (e.g., the anti-PD-L1 antibody or the compound of formula (I)) or the pharmaceutical combinations thereof disclosed herein and a pharmaceutically acceptable excipient. The pharmaceutical composition is intended to facilitate the administration of the compound or the pharmaceutical combination thereof disclosed herein to a subject. As used herein, the terms "pharmaceutical composition" and "formulation" have the same meaning and are used interchangeably.

Administration

The content below is not intended to limit the administration of the pharmaceutical combination disclosed herein. The components in the pharmaceutical combination disclosed herein can be formulated separately, or some or all of the components are co-formulated. In one embodiment, the pharmaceutical combination disclosed herein can be formulated into a pharmaceutical composition which is suitable for a single dose or multiple doses.

The components in the pharmaceutical combination disclosed herein can be administered separately, or some or all of the components are co-administered. The components in the pharmaceutical combination disclosed herein can be administered in a substantially asynchronous manner, or some or all of the components are administered in a substantially synchronous manner.

The components in the pharmaceutical combination disclosed herein can be administered independently, or some or all of the components are co-administered in various proper routes, including, but not limited to, oral administration or parenteral administration (by intravenous, intramuscular, local or subcutaneous routes). In some embodiments, the components in the pharmaceutical combination disclosed herein can be administered independently, or some or all of the components are co-administered by oral administration or injection, for example, intravenous injection or intraperitoneal injection.

The components in the pharmaceutical combination disclosed herein can be formulated independently in suitable dosage forms, or some or all of the components are co-formulated in a suitable dosage form including, but not limited to, tablet, lozenge, pill, capsule (for example, hard capsule, soft capsule, enteric capsule and microcapsule), elixir, granule, syrup, injection (intramuscular, intravenous and intraperitoneal), granule, emulsion, suspension, solution, dispersant and dosage forms of sustained-released formulations for oral or non-oral administration.

The components in the pharmaceutical combination disclosed herein can be formulated independently, or some or all of the components are co-formulated with a pharmaceutically acceptable carrier and/or excipient.

The pharmaceutical combination disclosed herein may further comprise an additional therapeutic agent. In one embodiment, the additional therapeutic agent can be a known therapeutic agent for cancer in the art.

DETAILED DESCRIPTION

The present disclosure is further described below with reference to specific examples, which, however, are only for illustration and do not limit the scope of the present disclosure. Likewise, the present disclosure is not limited to any specific preferred embodiment described herein. It should be appreciated by those skilled in the art that equivalent substitutions or corresponding modifications made to the technical features of the present disclosure still fall within the scope of the present disclosure. Unless otherwise stated, the reagents used in the following examples are commercially available products, and the solutions can be prepared by conventional techniques in the art.

TABLE 1

| List of abbreviations | |
|---|---|
| Abbreviation | Chinese full name |
| AE | Adverse event |
| ANOVA | Analysis of variance |
| AUC | Area under plasma concentration-time curve |
| AUCss | Area under steady-state plasma concentration-time curve |
| CFDA | National Medical Products Administration |
| CL | Apparent clearance |
| $C_{max}$ | Maximum plasma concentration observed |
| $C_{ss-max}$ | Steady-state peak concentration |
| $C_{ss-min}$ | Steady-state trough concentration |
| $C_{ss-av}$ | Mean steady-state plasma concentration |
| CTCAE | Common Terminology Criteria for Adverse Events |

TABLE 1-continued

List of abbreviations

| Abbreviation | Chinese full name |
|---|---|
| DCR | Disease control rate |
| dMMR | Deletion of mismatch repair gene |
| DOR | Duration of response |
| DLT | Dose limiting toxicity |
| GCP | Good clinical practice |
| HED | Human equivalent dose |
| LLOQ | Lower limit of quantitation |
| MTD | Maximum tolerated dose |
| MSI-H | Microsatellite instability-high |
| NOAEL | No observed adverse effect level |
| ORR | Objective response rate |
| PFS | Progression-free survival |
| ECOG PS | Eastern Cooperative Oncology Group-performance status |
| ALT | Alanine aminotransferase (alanine transaminase) |
| AST | Aspartate aminotransferase (aspartate transaminase) |
| TB | Total bilirubin |
| DB | Direct bilirubin |
| BUN | Urea |
| Cr | Creatinine |
| CT | X-ray computed tomography |
| MRI | Nuclear magnetic resonance |
| QTc | Corrected Q-T interval |
| HBsAg | Hepatitis B surface antigen |
| HBV DNA | Hepatitis B |
| HCV | Hepatitis C |
| OS | Overall survival |
| SAE | Severe adverse event |
| SD | Stable disease |
| PD | Disease progression |
| SOP | Standard operating procedure |
| TMB | Tumor mutational burden |
| $t_{1/2}$ | Time required for plasma concentration to be reduced by half |
| $T_{max}$ | Time to peak concentration observed |
| TTR | Time to response |
| $V_d$ | Apparent volume of distribution |
| NYHA | New York Heart Disease Association |

Response Evaluation Criteria (Evaluation of Therapeutic Efficacy According to RECIST 1.1/iRECIST Evaluation Criteria)

PFS (progression-free survival): first dose to disease progression or death (whichever occurred first).

ORR (objective response rate): proportion of subjects with confirmed disease assessed as CR+PR.

DCR (disease control rate): proportion of patients whose tumors shrink or remain stable for a certain period of time, including cases of CR, PR and SD.

DoR (duration of response): for patients whose optimal response is complete or partial response, defined as the time from the first occurrence of CR or PR to disease progression or relapse or death from all causes; for subjects who achieve response and do not have disease progression or a recurrence or do not die from various causes prior to analysis, the time of the last disease assessment is counted as an end.

CR (complete response): all target lesions disappear.

PR (partial response): the total diameter of the target lesion is reduced by 30% or more.

PD (disease progression): the total diameter of the target lesion is increased by 20% or more than the minimum value of the total diameter in the research, and the absolute value of the total diameter is increased by 5 mm or more; or one or more new lesions occur.

SD (stable disease): the target lesion is reduced and does not reach the PR standard; or the target lesion is enlarged and does not reach the PD standard.

The total diameter of the target lesion is the sum of the diameters of the target lesion (including the long diameter of the lesion and the short diameter of the lymph node).

Example 1: Treatment of Liver Cancer with Combined Pharmaceutical Composition of c-Met Kinase Inhibitor and Anti-PD-L1 Antibody 1. Inclusion Criteria and Treatment Regimen 1.1. Inclusion Criteria 1) Aged 18-75 years; ECOG PS score: 0-1; an expected survival time ≥3 months;

2) Patients who have been histopathologically or cytologically diagnosed with hepatocellular carcinoma;

3) Patients with hepatocellular carcinoma need to meet the following criteria:

(1) having not received any systemic treatment for HCC;

(2) subjects with Barcelona clinic liver cancer stage (BCLC stage) C, or subjects with stage B that are not suitable for local treatment or are refractory to local treatment, and are not suitable for treatment with radical therapy;

(3) with Child-Pugh liver function grade A;

(4) patients after local treatment (including but not limited to surgery, TACE, TAI, radiofrequency or microwave ablation, absolute alcohol injection) should be at least 4 weeks after the end of local treatment and have recovered sufficiently from treatment toxicity and/or complications to be enrolled;

4) Central nervous system metastasis without clinical symptoms or with clinical symptoms and the disease is controlled and stable for ≥4 weeks after treatment;

5) HBVDNA quantification must be <500 IU/mL or 2500 copies/mL, and patients in need of treatment receive anti-HBV treatment for at least 2 weeks prior to the study and are willing to receive anti-viral treatment throughout the study according to Guidelines for the Prevention and Treatment of Chronic Hepatitis B (2019 Edition); patients with positive HCVRNA quantification must complete anti-viral treatment at least 1 month prior to the study;

6) Having at least one measurable lesion (RECIST 1.1);

7) Normal main organ functions meeting the following criteria:

(1) the blood routine examination criteria to be met: a) hemoglobin ≥90 g/L; b) absolute neutrophil count ≥1.5×10$^9$/L; and c) platelet count ≥75×10$^9$/L (no transfusion of blood or blood products, no correction using granulocyte colony-stimulating factor and drugs within 14 days);

(2) biochemical test needs to meet the following criteria: a) albumin ≥30 g/L (no transfusion of albumin or blood products within 14 days); b) ALT and AST<5.0×upper limit of normal (ULN); total bilirubin ≤2×ULN; and c) serum creatinine ≤1.5×ULN or creatinine clearance (Ccr)>50 mL/min (Cockcroft-Gault equation: Ccr=(140−age)×weight (Kg)/72×Scr (mg/dl) or Ccr=(140−age)×weight (Kg)/0.818×Scr (umol/L), calculation result×0.85 for a female);

(3) prothrombin time (PT) is prolonged by ≤3 s compared with the upper limit of normal;

8) Radiotherapy for bone metastases accompanied by clinical symptoms must be completed at least 2 weeks prior to the study;

9) Female subjects of childbearing age should agree to take contraceptive measures (such as intrauterine devices, contraceptives or condoms) during the study and for 6 months after the study; serum pregnancy test results should be negative within 7 days before enrollment, and the subjects must not be breastfeeding; male subjects should agree to take contraceptive measures during the study and for 6 months after the study;

10) Voluntary participation, written informed consent and good compliance.

1.2. Test Compounds

Compound of formula (I) capsules: strength: 30 mg/capsule and 60 mg/capsule, provided by Chia Tai Tianqing Pharmaceutical Group Co., Ltd.

hu5G11-hIgG1 injection: strength: 100 mg/10 mL and 600 mg/20 mL, provided by Chia Tai Tianqing Pharmaceutical Group Co., Ltd.

1.3. Administration Regimen

Regimen A: compound of formula (I) capsules 120 mg/qd+ hu5G11-hIgG1 1200 mg (the first day)

Regimen B: compound of formula (I) capsules 150 mg/qd+ hu5G11-hIgG1 1200 mg (the first day)

1.4. Administration Methods hu5G11-hIgG1 injection: diluted to 250 mL with 1200 mg of normal saline, the infusion time was 60±5 min, the injection was administered once every 21 days, and 21 days was counted as 1 administration cycle.

Compound of formula (I) capsules: continuously administered once daily (within ±5 min of starting infusion of hu5G11-hIgG1 injection on an empty stomach). Except in special circumstances, it was recommended to take it at a fixed time every day. 21 days was counted as an administration cycle.

1.5. Evaluation Criteria

The main efficacy indicators were evaluated according to the RECIST1.1 criteria.

2. Results 2.1. Pre-Treatment Diagnosis and Treatment History

Clinical Diagnosis of Patient A:

(1) clinical diagnosis-primary site: hepatocellular carcinoma, moderately differentiated.

(2) TNM stage: T3bN0M0

(3) clinical stage: stage IIIB (4) BCLC stage: stage B

Treatment History Before Treatment:

(1) surgery history: no (2) history of chemotherapy and anti-tumor drug therapy: no (3) history of radiotherapy: no 2.2. Treatment Regimen For patient A, the following treatment regimen, shown in regimen A, was used:

compound of formula (I) capsules 120 mg/qd+hu5G11-hIgG1 1200 mg (the first day)

2.3. Response and Evaluation

For patient A, the response and evaluation were as follows:

screening phase (before treatment phase): target lesion: 108 mm;

2 cycles of treatment: target lesion: 82 mm;

4 cycles of treatment: target lesion: 75 mm;

6 cycles of treatment: target lesion: 76 mm;

8 cycles of treatment: target lesion: 73 mm;

10 cycles of treatment: target lesion: 86 mm.

The best response for patient A was PR (partial response) according to the Response Evaluation Criteria.

Example 2: Treatment of Gastric Cancer with Combined Pharmaceutical Composition of c-Met Kinase Inhibitor and Anti-PD-L1 Antibody 1. Inclusion Criteria and Treatment Regimen 1.1. Inclusion Criteria 1) Aged 18-75 years; ECOG PS score: 0-1; an expected survival time ≥3 months;

2) Patients who have been histopathologically or cytologically diagnosed with gastric adenocarcinoma/gastroesophageal junction adenocarcinoma;

3) Patients with advanced gastric adenocarcinoma/gastroesophageal junction adenocarcinoma that are not suitable for surgery and have failed first-line standard chemotherapy (no less than 2 cycles of treatment) need to meet any of the following criteria:

(1) having disease progression during the first-line treatment of the gastric cancer, or within 4 months after the end of treatment after the last administration (including maintenance monotherapy for the first-line treatment);

(2) having a recurrence or metastasis during neoadjuvant or adjuvant therapy or within 6 months after the last administration, which is considered failure of first-line systemic chemotherapy for the progressive disease;

4) Central nervous system metastasis without clinical symptoms or with clinical symptoms and the disease is controlled and stable for ≥4 weeks after treatment;

5) HBVDNA quantification must be <500 IU/mL or 2500 copies/mL, and patients in need of treatment receive anti-HBV treatment for at least 2 weeks prior to the study and are willing to receive anti-viral treatment throughout the study according to Guidelines for the Prevention and Treatment of Chronic Hepatitis B (2019 Edition); patients with positive HCVRNA quantification must complete anti-viral treatment at least 1 month prior to the study;

6) Having at least one measurable lesion (RECIST 1.1);

7) Normal main organ functions meeting the following criteria:

(1) the blood routine examination criteria to be met: a) hemoglobin ≥90 g/L; b) absolute neutrophil count ≥1.5×10$^9$/L; and c) platelet count ≥75×10$^9$/L (no transfusion of blood or blood products, no correction using granulocyte colony-stimulating factor and drugs within 14 days);

(2) biochemical test needs to meet the following criteria: a) albumin ≥30 g/L (no transfusion of albumin or blood products within 14 days); b) ALT and AST<3.0×upper limit of normal (ULN); total bilirubin ≤2×ULN; and c) serum creatinine ≤1.5×ULN or creatinine clearance (Ccr)>50 mL/min (Cockcroft-Gault equation: Ccr=(140−age)×weight (Kg)/72×Scr (mg/dl) or Ccr=(140−age)×weight (Kg)/0.818×Scr (umol/L), calculation result×0.85 for a female);

(3) prothrombin time (PT) is prolonged by ≤3 s compared with the upper limit of normal;

8) Radiotherapy for bone metastases accompanied by clinical symptoms must be completed at least 2 weeks prior to the study;

9) Female subjects of childbearing age should agree to take contraceptive measures (such as intrauterine devices, contraceptives or condoms) during the study and for 6 months after the study; serum pregnancy test results should be negative within 7 days before enrollment, and the subjects must not be breastfeeding; male subjects should agree to take contraceptive measures during the study and for 6 months after the study;

10) Voluntary participation, written informed consent and good compliance.

1.2. Test Compounds

Compound of formula (I) capsules: strength: 30 mg/capsule and 60 mg/capsule, provided by Chia Tai Tianqing Pharmaceutical Group Co., Ltd.

hu5G11-hIgG1 injection: strength: 100 mg/10 mL and 600 mg/20 mL, provided by Chia Tai Tianqing Pharmaceutical Group Co., Ltd.

1.3. Administration Regimen

Regimen A: compound of formula (I) capsules 120 mg/qd+hu5G11-hIgG1 1200 mg (the first day)

Regimen B: compound of formula (I) capsules 150 mg/qd+hu5G11-hIgG1 1200 mg (the first day)

1.4. Administration Methods hu5G11-hIgG1 injection: diluted to 250 mL with 1200 mg of normal saline, the infusion time was 60±5 min, the injection was administered once every 21 days, and 21 days was counted as 1 administration cycle.

Compound of formula (I) capsules: continuously administered once daily (within ±5 min of starting infusion of hu5G11-hIgG1 injection on an empty stomach). Except in special circumstances, it was recommended to take it at a fixed time every day. 21 days was counted as an administration cycle.

1.5. Evaluation Criteria

The main efficacy indicators were evaluated according to the RECIST1.1 criteria.

2. Results 2.1. Pre-Treatment Diagnosis and Treatment History 2.1.1. Clinical Diagnosis and Treatment History of Patient B (1) (Gastric) adenocarcinoma, moderately-poorly differentiated, pTNM stage: pT3N3. Immunohistochemistry showed that: i. HER-2(−), Ki67 (+ about 60%), MLH1 (+), MSH2 (+), PMS2 (+), MSH6 (+), SYN (−); ii. proximal resection margin, distal resection margin, greater omentum (−); iii. lymph node showed cancer metastasis (14/18); lesser curvature tissue (−), greater curvature (2/3), region 1 tissue (−), region 3a (0/1), region 4 (2/2), region 5 (2/2), region 6 (5/5), region 7 tissue (−), region 8a (3/4), region 9 (0/1), region 12a tissue (−), and region 14v tissue (−).

(2) Radical gastrectomy was performed after the diagnosis. After radical surgery, XELOX regimen (oxaliplatin in combination with capecitabine) was used for 8 cycles of chemotherapy, followed by maintenance therapy with oxaliplatin.

2.1.2. Clinical Diagnosis and Treatment History of Patient C (1) Advanced gastric cancer, adenocarcinoma found in both fundus and body of stomach, hepatogastric ligament and retroperitoneal lymph node metastases and right upper arm metastases. Immunohistochemistry (fundus of stomach) showed: BRAF V600E (−), HER-2 (1+), PMS2 (+), MLH1 (+), MSH2 (+), MSH6

(+), and AFP (+). (2) Chemotherapy was performed for 8 cycles with DOS regimen (docetaxel and oxaliplatin in combination with tegafur-gimeracil-oteracil potassium) after diagnosis, followed by maintenance therapy with tegafur-gimeracil-oteracil potassium.

2.2. Treatment Regimen

For both patient B and patient C, the treatment regimen was as follows:

Regimen A: compound of formula (I) capsules 120 mg/qd+hu5G11-hIgG1 1200 mg (the first day)

2.3. Response and Evaluation 2.3.1. For Patient B, the Response and Evaluation were as Follows:

screening phase (before treatment phase): target lesion: 45.21 mm;

2 cycles of treatment: target lesion: 42.79 mm;

4 cycles of treatment: target lesion: 30.85 mm;

6 cycles of treatment: target lesion: 30.08 mm;

8 cycles of treatment: target lesion: 35.06 mm;

10 cycles of treatment: target lesion: 38.13 mm.

The best response for patient B was PR (partial response) according to the Response Evaluation Criteria.

2.3.2. For Patient C, the Response and Evaluation were as Follows:

screening phase (before treatment phase): target lesion: 18.6 mm;

2 cycles of treatment: target lesion: 14.3 mm;

4 cycles of treatment: target lesion: 12.0 mm;

6 cycles of treatment: target lesion: 14.0 mm;

8 cycles of treatment: target lesion: 14.2 mm.

The best response for patient C was PR (partial response) according to the Response Evaluation Criteria.

All technical features of the present disclosure may be combined in any way. Each feature of the present disclosure may also be replaced by other features that have the same, equivalent or similar effects. Thus, unless otherwise stated, each feature disclosed is only an example of a series of equivalent or similar features.

Furthermore, those skilled in the art can readily understand the key features of the present disclosure according to the above description. Many modifications can be made to the present invention without departing from the spirit and scope of the present disclosure so the present invention is suitable for a variety of purposes and conditions of use, and therefore such modifications are also intended to fall within the scope of the appended claim.

Herein incorporated by reference is the sequence listing filed with the USPTO as 1140-006 NATL_ST25.txt which was created on May 10, 2023, and the size is 22,406 bytes.

---

The invention claimed is:

1. A combined pharmaceutical composition, comprising: an anti-PD-L1 antibody and a compound of formula (I) or a pharmaceutically acceptable salt thereof, formula (I)

wherein the anti-PD-L1 antibody comprises the following amino acid sequences:

a heavy chain CDR1 region consisting of the amino acid sequence set forth in SEQ ID NO:1;

a heavy chain CDR2 region consisting of the amino acid sequence set forth in SEQ ID NO:2;

a heavy chain CDR3 region consisting of the amino acid sequence set forth in SEQ ID NO:3;

a light chain CDR1 region consisting of the amino acid sequence set forth in SEQ ID NO:7;

a light chain CDR2 region consisting of the amino acid sequence set forth in SEQ ID NO:8; and a light chain CDR3 region consisting of the amino acid sequence set forth in SEQ ID NO:9.

2. The combined pharmaceutical composition of claim 1, wherein the anti-PD-L1 antibody and the compound of formula (I) or the pharmaceutically acceptable salt thereof are each in the form of a pharmaceutical composition.

3. A kit of pharmaceutical compositions for treating cancer, comprising:

(a) a first pharmaceutical composition comprising an anti-PD-L1 antibody of claim 1 as an active ingredient; and (b) a second pharmaceutical composition comprising a compound of formula (I) or a pharmaceutically acceptable salt thereof of claim 1 as an active ingredient.

4. A method for treating cancer, comprising:

administering to a subject suffering from cancer a therapeutically effective amount of the combined pharmaceutical composition according to claim 1.

5. The method of claim 4, wherein the anti-PD-L1 antibody is continuously administered at one or more flat doses of about 20 mg to about 2400 mg.

6. The method of claim 4, wherein the compound of formula (I) or the pharmaceutically acceptable salt thereof is administered at a dose of 90 mg to 180 mg.

7. The method of claim 4, wherein the compound of formula (I) or the pharmaceutically acceptable salt thereof is administered in combination with the anti-PD-L1 antibody in 21-day treatment cycles, and the administration is done by administering by infusion 1200 mg of the anti-PD-L1 antibody over a period of 60±5 min on the first day, and administering 120 mg or 150 mg of the compound of formula (I) or the pharmaceutically acceptable salt thereof once daily over 21 consecutive days.

8. The method of claim 4, wherein the cancer is liver cancer or gastric cancer.

9. The method of claim 8, wherein the liver cancer is hepatocellular carcinoma.

10. The method of claim 8, wherein the gastric cancer is gastric adenocarcinoma or gastroesophageal junction adenocarcinoma.

11. The combined pharmaceutical composition of claim 1, wherein the anti-PD-L1 antibody comprises:

the heavy chain variable region set forth in SEQ ID NO:13 and the light chain variable region set forth in SEQ ID NO:15.

12. The combined pharmaceutical composition of claim 1, wherein the anti-PD-L1 antibody comprises:

the heavy chain amino acid sequence set forth in SEQ ID NO: 17 and the light chain amino acid sequence set forth in SEQ ID NO: 18.

13. The method of claim 5, wherein the anti-PD-L1 antibody is continuously administered at a flat dose of about 1200 mg.

14. The method of claim 5, wherein the anti-PD-L1 antibody is administered once every 21 days.

15. The method of claim 6, wherein the compound of formula (I) or the pharmaceutically acceptable salt thereof is administered at a dose of 120 mg or 150 mg.

16. The method of claim 6, wherein the compound of formula (I) or the pharmaceutically acceptable salt thereof is administered once daily.

17. A method for treating cancer, comprising:

administering to a subject suffering from cancer a therapeutically effective amount of (1) a compound of formula (I) or a pharmaceutically acceptable salt thereof, formula (I)

and (2) an anti-PD-L1 antibody, wherein the anti-PD-L1 antibody comprises the following amino acid sequences:

a heavy chain CDR1 region consisting of the amino acid sequence set forth in SEQ ID NO:1;

a heavy chain CDR2 region consisting of the amino acid sequence set forth in SEQ ID NO:2;

a heavy chain CDR3 region consisting of the amino acid sequence set forth in SEQ ID NO:3;

a light chain CDR1 region consisting of the amino acid sequence set forth in SEQ ID NO:7;

a light chain CDR2 region consisting of the amino acid sequence set forth in SEQ ID NO:8; and a light chain CDR3 region consisting of the amino acid sequence set forth in SEQ ID NO:9, wherein the anti-PD-L1 antibody is administered at one or more flat doses of about 20 mg to about 2400 mg.

18. The method of claim 17, wherein the compound of formula (I) or the pharmaceutically acceptable salt thereof is administered at a dose of 90 mg to 180 mg.

19. The method of claim 17, wherein the anti-PD-L1 antibody comprises:

the heavy chain variable region set forth in SEQ ID NO: 13 and the light chain variable region set forth in SEQ ID NO:15.

20. The method of claim 17, wherein the anti-PD-L1 antibody comprises:

the heavy chain amino acid sequence set forth in SEQ ID NO: 17 and the light chain amino acid sequence set forth in SEQ ID NO: 18.

* * * * *

SEQUENCE LISTING

```
<160> NUMBER OF SEQ ID NOS: 21

<210> SEQ ID NO 1
<211> LENGTH: 5
<212> TYPE: PRT
<213> ORGANISM: Mus sp.

<400> SEQUENCE: 1

Thr Tyr Gly Val His
1               5

<210> SEQ ID NO 2
<211> LENGTH: 16
<212> TYPE: PRT
```

-continued

```
<213> ORGANISM: Mus sp.

<400> SEQUENCE: 2

Val Ile Trp Arg Gly Val Thr Thr Asp Tyr Asn Ala Ala Phe Met Ser
1               5                   10                  15

<210> SEQ ID NO 3
<211> LENGTH: 8
<212> TYPE: PRT
<213> ORGANISM: Mus sp.

<400> SEQUENCE: 3

Leu Gly Phe Tyr Ala Met Asp Tyr
1               5

<210> SEQ ID NO 4
<211> LENGTH: 5
<212> TYPE: PRT
<213> ORGANISM: Mus sp.

<400> SEQUENCE: 4

Ser Tyr Gly Met Ser
1               5

<210> SEQ ID NO 5
<211> LENGTH: 16
<212> TYPE: PRT
<213> ORGANISM: Mus sp.

<400> SEQUENCE: 5

Ser Ile Ser Ser Gly Gly Ser Thr Tyr Tyr Pro Asp Ser Val Lys Gly
1               5                   10                  15

<210> SEQ ID NO 6
<211> LENGTH: 8
<212> TYPE: PRT
<213> ORGANISM: Mus sp.

<400> SEQUENCE: 6

Gly Tyr Asp Ser Gly Phe Ala Tyr
1               5

<210> SEQ ID NO 7
<211> LENGTH: 11
<212> TYPE: PRT
<213> ORGANISM: Mus sp.

<400> SEQUENCE: 7

Lys Ala Ser Gln Ser Val Ser Asn Asp Val Ala
1               5                   10

<210> SEQ ID NO 8
<211> LENGTH: 7
<212> TYPE: PRT
<213> ORGANISM: Mus sp.

<400> SEQUENCE: 8

Tyr Ala Ala Asn Arg Tyr Thr
1               5

<210> SEQ ID NO 9
<211> LENGTH: 9
<212> TYPE: PRT
<213> ORGANISM: Mus sp.
```

-continued

```
<400> SEQUENCE: 9

Gln Gln Asp Tyr Thr Ser Pro Tyr Thr
1               5

<210> SEQ ID NO 10
<211> LENGTH: 14
<212> TYPE: PRT
<213> ORGANISM: Mus sp.

<400> SEQUENCE: 10

Ala Ser Gln Ser Val Ser Thr Ser Ser Ser Ser Phe Met His
1               5                   10

<210> SEQ ID NO 11
<211> LENGTH: 7
<212> TYPE: PRT
<213> ORGANISM: Mus sp.

<400> SEQUENCE: 11

Tyr Ala Ser Asn Leu Glu Ser
1               5

<210> SEQ ID NO 12
<211> LENGTH: 9
<212> TYPE: PRT
<213> ORGANISM: Mus sp.

<400> SEQUENCE: 12

Gln His Ser Trp Glu Ile Pro Tyr Thr
1               5

<210> SEQ ID NO 13
<211> LENGTH: 116
<212> TYPE: PRT
<213> ORGANISM: Artificial sequence
<220> FEATURE:
<223> OTHER INFORMATION: Heavy chain variable regions of hu5G11-hIgG1
      and hu5G11-hIgG4

<400> SEQUENCE: 13

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
                20                  25                  30

Gly Val His Trp Ile Arg Gln Pro Pro Gly Lys Ala Leu Glu Trp Leu
            35                  40                  45

Gly Val Ile Trp Arg Gly Val Thr Thr Asp Tyr Asn Ala Ala Phe Met
        50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser
        115

<210> SEQ ID NO 14
<211> LENGTH: 116
<212> TYPE: PRT
<213> ORGANISM: Artificial sequence
<220> FEATURE:
```

-continued

<223> OTHER INFORMATION: Heavy chain variable regions of hu13C5-hIgG1
     and hu13C5-hIgG4

<400> SEQUENCE: 14

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser
        115
```

<210> SEQ ID NO 15
<211> LENGTH: 107
<212> TYPE: PRT
<213> ORGANISM: Artificial sequence
<220> FEATURE:
<223> OTHER INFORMATION: Light chain variable regions of hu5G11-hIgG1
     and hu5G11-hIgG4

<400> SEQUENCE: 15

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys
            100                 105
```

<210> SEQ ID NO 16
<211> LENGTH: 111
<212> TYPE: PRT
<213> ORGANISM: Artificial sequence
<220> FEATURE:
<223> OTHER INFORMATION: Light chain variable regions of hu13C5-hIgG1
     and hu13C5-hIgG4

<400> SEQUENCE: 16

```
Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
```

-continued

```
              35                    40                    45
Lys Leu Leu Ile Lys Tyr Ala Ser Asn Leu Glu Ser Gly Val Pro Ala
    50                    55                    60

Arg Phe Ser Gly Ser Gly Ser Gly Thr Asp Phe Thr Leu Thr Ile Asn
65                    70                    75                    80

Pro Val Glu Ala Asn Asp Thr Ala Asn Tyr Tyr Cys Gln His Ser Trp
                  85                    90                    95

Glu Ile Pro Tyr Thr Phe Gly Gln Gly Thr Lys Leu Glu Ile Lys
                  100                   105                   110

<210> SEQ ID NO 17
<211> LENGTH: 446
<212> TYPE: PRT
<213> ORGANISM: Artificial sequence
<220> FEATURE:
<223> OTHER INFORMATION: Heavy chain of hu5G11-hIgG1

<400> SEQUENCE: 17

Gln Ile Thr Leu Lys Glu Ser Gly Pro Thr Leu Val Lys Pro Thr Gln
1                 5                     10                    15

Thr Leu Thr Leu Thr Cys Thr Val Ser Gly Phe Ser Leu Ser Thr Tyr
                  20                    25                    30

Gly Val His Trp Ile Arg Gln Pro Pro Gly Lys Ala Leu Glu Trp Leu
              35                    40                    45

Gly Val Ile Trp Arg Gly Val Thr Thr Asp Tyr Asn Ala Ala Phe Met
    50                    55                    60

Ser Arg Leu Thr Ile Thr Lys Asp Asn Ser Lys Asn Gln Val Val Leu
65                    70                    75                    80

Thr Met Asn Asn Met Asp Pro Val Asp Thr Ala Thr Tyr Tyr Cys Ala
                  85                    90                    95

Arg Leu Gly Phe Tyr Ala Met Asp Tyr Trp Gly Gln Gly Thr Leu Val
                  100                   105                   110

Thr Val Ser Ser Ala Ser Thr Lys Gly Pro Ser Val Phe Pro Leu Ala
              115                   120                   125

Pro Ser Ser Lys Ser Thr Ser Gly Gly Thr Ala Ala Leu Gly Cys Leu
              130                   135                   140

Val Lys Asp Tyr Phe Pro Glu Pro Val Thr Val Ser Trp Asn Ser Gly
145                   150                   155                   160

Ala Leu Thr Ser Gly Val His Thr Phe Pro Ala Val Leu Gln Ser Ser
                  165                   170                   175

Gly Leu Tyr Ser Leu Ser Ser Val Val Thr Val Pro Ser Ser Ser Leu
                  180                   185                   190

Gly Thr Gln Thr Tyr Ile Cys Asn Val Asn His Lys Pro Ser Asn Thr
              195                   200                   205

Lys Val Asp Lys Lys Val Glu Pro Lys Ser Cys Asp Lys Thr His Thr
    210                   215                   220

Cys Pro Pro Cys Pro Ala Pro Glu Leu Leu Gly Gly Pro Ser Val Phe
225                   230                   235                   240

Leu Phe Pro Pro Lys Pro Lys Asp Thr Leu Met Ile Ser Arg Thr Pro
                  245                   250                   255

Glu Val Thr Cys Val Val Val Ala Val Ser His Glu Asp Pro Glu Val
                  260                   265                   270

Lys Phe Asn Trp Tyr Val Asp Gly Val Glu Val His Asn Ala Lys Thr
                  275                   280                   285

Lys Pro Arg Glu Glu Gln Tyr Asn Ser Thr Tyr Arg Val Val Ser Val
```

-continued

```
            290                 295                 300
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 18
<211> LENGTH: 214
<212> TYPE: PRT
<213> ORGANISM: Artificial sequence
<220> FEATURE:
<223> OTHER INFORMATION: Light chains of hu5G11-hIgG1 and hu5G11-hIgG4

<400> SEQUENCE: 18

Asp Ile Gln Met Thr Gln Ser Pro Ser Ser Leu Ser Ala Ser Val Gly
1                   5                   10                  15

Asp Arg Val Thr Ile Thr Cys Lys Ala Ser Gln Ser Val Ser Asn Asp
                20                  25                  30

Val Ala Trp Tyr Gln Gln Lys Pro Gly Lys Ala Pro Lys Leu Leu Ile
                35                  40                  45

Tyr Tyr Ala Ala Asn Arg Tyr Thr Gly Val Pro Asp Arg Phe Ser Gly
            50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
```

```
       210

<210> SEQ ID NO 19
<211> LENGTH: 446
<212> TYPE: PRT
<213> ORGANISM: Artificial sequence
<220> FEATURE:
<223> OTHER INFORMATION: Heavy chain of hu13C5-hIgG1

<400> SEQUENCE: 19

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
```

-continued

```
                355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 20
<211> LENGTH: 218
<212> TYPE: PRT
<213> ORGANISM: Artificial sequence
<220> FEATURE:
<223> OTHER INFORMATION: Light chain of hu13C5-hIgG1

<400> SEQUENCE: 20

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
            35                  40                  45

Lys Leu Leu Ile Lys Tyr Ala Ser Asn Leu Glu Ser Gly Val Pro Ala
        50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 21
<211> LENGTH: 442
<212> TYPE: PRT
<213> ORGANISM: Artificial sequence
<220> FEATURE:
<223> OTHER INFORMATION: Heavy chain of hu5G11-hIgG4

<400> SEQUENCE: 21
```

-continued

```
Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Pro Gly Lys Ala Leu Glu Trp Leu
            35                  40                  45

Gly Val Ile Trp Arg Gly Val Thr Thr Asp Tyr Asn Ala Ala Phe Met
        50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
        210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
            325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
            405                 410                 415

Asn Val Phe Ser Cys Ser Val Met His Glu Ala Leu His Asn His Tyr
```

-continued

| | 420 | | | | 425 | | | 430 | |
|---|---|---|---|---|---|---|---|---|---|

Thr Gln Lys Ser Leu Ser Leu Ser Leu Gly
        435                    440